US008347738B2

(12) United States Patent
Tung et al.

(10) Patent No.: US 8,347,738 B2
(45) Date of Patent: Jan. 8, 2013

(54) SENSORS AND CONTROL FOR AN INTERVENTIONAL CATHETER

(75) Inventors: Alexander Tung, Mountain View, CA (US); Günter Niemeyer, Mountain View, CA (US); David Liang, Menlo Park, CA (US); Byong-Ho Park, Cincinnati, OH (US); Friedrich B. Prinz, Woodside, CA (US); Bob S. Hu, Stanford, CA (US)

(73) Assignee: The Board of Trustees of the Leland Stanford Junior University, Palo Alto, CA (US)

( * ) Notice: Subject to any disclaimer, the term of this patent is extended or adjusted under 35 U.S.C. 154(b) by 1161 days.

(21) Appl. No.: 12/151,963

(22) Filed: May 9, 2008

(65) Prior Publication Data

US 2009/0099551 A1    Apr. 16, 2009

Related U.S. Application Data

(60) Provisional application No. 60/928,606, filed on May 9, 2007.

(51) Int. Cl.
*G01L 1/22* (2006.01)
(52) U.S. Cl. .......................................................... 73/862
(58) Field of Classification Search ...................... 73/862
See application file for complete search history.

(56) References Cited

U.S. PATENT DOCUMENTS

| 4,977,886 A | | 12/1990 | Takehana et al. | |
|---|---|---|---|---|
| 5,807,265 A | * | 9/1998 | Itoigawa et al. | 600/486 |
| 6,287,292 B1 | * | 9/2001 | Fariabi | 604/531 |
| 6,622,558 B2 | * | 9/2003 | Huff et al. | 73/432.1 |
| 7,073,387 B2 | * | 7/2006 | Zdeblick et al. | 73/715 |
| 7,481,774 B2 | * | 1/2009 | Brockway et al. | 600/561 |
| 7,527,594 B2 | * | 5/2009 | Vardi et al. | 600/467 |
| 7,660,492 B2 | * | 2/2010 | Bates et al. | 385/7 |
| 7,930,065 B2 | * | 4/2011 | Larkin et al. | 700/245 |
| 8,048,063 B2 | * | 11/2011 | Aeby et al. | 606/1 |
| 2007/0133925 A1 | | 6/2007 | Bates et al. | |
| 2008/0294144 A1 | * | 11/2008 | Leo et al. | 604/508 |

OTHER PUBLICATIONS

Hidek Nagai Amd Ryutaro Oishi, Shape memory alloys as strain sensors in composites, Apr. 20, 2005, 493-4982006 IOP Published Ltd UK.
S.H. Nahm, Y.I. Kim, J.M.Kim ans D.J. Yoon, A study on the application of Ni—Ti shape memory Alloy as a Sensor, 2043-2046, vol. 475-479(2005) Switzerland.

* cited by examiner

*Primary Examiner* — Lisa Caputo
*Assistant Examiner* — Octavia Davis-Hollington
(74) *Attorney, Agent, or Firm* — Lumen Patent Firm

(57) ABSTRACT

This invention provides small position sensors for applications where localized sensing in a small volume of space is needed but where measurement of large relative displacement is also necessary. The invention enables a surgeon to accurately position the tip of a catheter during minimally invasive therapy. The current invention further improves the quality of tactile feedback to a physician during catheter-based surgeries with an axial force sensor at the tip of the catheter that allows for the transmission of force information to the physician. One embodiment of this invention is a position sensor for active interventional catheters, where the sensor may be laser-machined shape memory alloy (SMA), and the catheter actuators may be heated SMA or wire-pulleys. Providing position feedback from a catheter during minimally invasive therapy allows for closed-loop control of the catheter tip position under computer-aided guidance and enable force feedback to the physician.

15 Claims, 29 Drawing Sheets

SENSORS AND CONTROL FOR AN INTERVENTIONAL CATHETER

CROSS-REFERENCE TO RELATED APPLICATIONS

This application is cross-referenced to and claims the benefit from U.S. Provisional Patent Application 60/928,606 filed May 9, 2007, which is hereby incorporated by reference.

STATEMENT REGARDING FEDERALLY SPONSORED RESEARCH OR DEVELOPMENT

The present invention was supported in part by grant number R21EB002826-01 from the The National Institutes of Health. The U.S. Government has certain rights in the invention.

FIELD OF THE INVENTION

The invention relates generally to interventional catheters. More particularly, the present invention relates to position sensors and force sensors for interventional catheters. The invention further relates to control of an interventional catheter during minimally invasive procedures.

BACKGROUND

Interventional medicine is seeing a growing trend toward minimally invasive and catheter-based therapy, especially in cardiovascular and intracardiac procedures. Minimally invasive therapy can greatly reduce patient trauma, recovery time, overall costs, and ultimately patient mortality and morbidity of procedures. Catheter-based interventions, as a form of minimally invasive surgery, can decrease hospitalization time and greatly lower patient morbidity compared to traditional methods. In cardiology, interventions are often performed using catheters to navigate through blood vessels to the heart starting from a small incision in the leg. The physician manipulates the catheter from outside the body by using pull cables along the flexible catheter. Percutaneous catheter procedures are hindered by a lack of precise tip manipulation when actuation forces are transmitted over the length of the catheter. These manual catheters lack the precision and dexterity needed to reach the desired locations inside the heart efficiently and effectively. Because pull cable forces must be translated along the length of the catheter, the translation of forces becomes overshadowed by friction and stiction along the catheter between the physician's hand and the catheter tip. Therefore, current catheters cannot match the manipulative capability or proprioceptive feedback that is available during more invasive open chest procedures.

In cardiology, accuracy in the range of a few mm is needed, where heart motion and flowing blood tend to perturb the position of the catheter tip. In addition, the catheter must be on the order of 3-4 mm in diameter to be able to navigate the blood vessels.

Development of a robotic or "active" catheter that can provide local, precise actuation relative to the tip of the catheter has the potential to overcome some of these challenges, but additional sensory information is necessary for precise control and force feedback. Shape memory alloy (SMA) actuators have a large force to volume ratio, thus making them an ideal candidate for minimally invasive tools. Unfortunately, the actuators also exhibit a large hysteresis, which makes them difficult to control, thus model-based open-loop control as well as feedback control using the SMA actuator's own electrical resistance have not led to reliable and controllable actuators, and were unable to provide measurement over the desired long-range of motion.

Current catheters do not have position sensing. In some cases the physician uses biplane fluoroscopy and manual manipulation to maneuver the catheter. Electronically actuated systems could improve the precision of manipulation, but feedback is still needed for good control. The need for position sensing is crucial to obtaining robust control of an active catheter. There are many position sensing techniques, but few are easily integrated into a catheter. Linear Variable Differential Transducers (LVDTs), capacitive sensors, and similar devices cannot be scaled down to a 2-3 mm diameter tubular structure required for intracardiac catheter applications.

The addition of separate position sensors can enable precise control of shape memory alloy (SMA) actuators. Active catheters with local SMA actuation can potentially provide the desired manipulation of a catheter tip, but to date a method does not exist to easily integrate small-volume compliant sensors to provide position and/or force feedback for the actuators. A number of research groups have attempted to build active catheter devices using different materials and methods. Some of these groups have used shape memory alloy actuators, but only one device has incorporated closed-loop feedback, and yet only limited success was achieved. Other devices rely on open-loop control of SMA actuators, which is challenging due to their large hysteresis.

Robotic or computer-aided surgical systems do not currently provide force information to the user. Although they have developed a master-slave user-interface for operation of their system, there is currently no ability to sense or feedback position of the catheter. Another group has developed a system for magnetic guidance of a catheter tip, but this system relies on large, bulky magnets to be placed within the interventional suite.

Currently it is very difficult to obtain force information from a catheter due to difficulty in integrating a small enough sensor on the tip of the catheter. Standard interventional catheters do not provide the physician with appreciable force feedback due to the inability of the catheter structure to effectively transmit forces from the tip down the length of a long floppy catheter to the physician. Current force sensors either cannot sense the small forces imparted on a catheter or do not fit the form factor or scale required for a sensor on a catheter. Even current robotic catheter systems cannot employ effective force sensors because there is no appropriate device that would fit on the end of a catheter.

The inventors have previously developed SMA actuators that were laser-machined from nitinol tubing to achieve up to 2N of force at 20% elongation, and have shown that if good position sensing is provided, the actuators can be controlled precisely regardless of their material properties. It is believed that these actuators are capable of exerting 500 mN forces over 500 µm, or up to 33% elongation. Therefore, development of a useful position sensor that can accurately detect this large change in elongation while providing little mechanical resistance becomes a challenge. External strain gauges are known to be difficult to mount on the actuator, and other sensor modalities, such as Hall Effect sensors, can be too costly, large, or complicated to implement. In addition, integration of separate technologies into this laser-machining platform is known to be difficult.

Because SMA actuators are highly nonlinear with large hysteresis, a method and device for obtaining feedback to control the actuators and achieve precise positioning is needed. Although there have been numerous attempts to use the resistance of the actuators themselves as position feedback, the nonlinear and hysteretic dependence of the resistance on both stress and temperature make it an elusive feedback variable. What is needed is a sensor that could be incorporated with an actuator, such as a SMA actuator or wire pulley actuator, and sense the actuators actual displacement directly to enable an accurately steerable mechanism. Local actuation of the catheter tip relative to a nearby reference point would provide the physician a higher degree of control. Furthermore, local position and force sensing would allow for closed-loop control of such an active catheter and better response to environmental perturbations. What is further needed is a system that incorporates position and force sensing along the length of the catheter, with the ability to actuate the catheter mechanically, and can provide sufficient force and dexterity as well as more accurate control of the catheter tip in an open environment like the heart chambers.

SUMMARY OF THE INVENTION

To address the deficiencies in the art, the current invention provides force and/or position sensing for active catheters. The invention includes at least one active interventional catheter, where the catheter has a first end and a second end such that the catheter first end is inserted to a body lumen an the second end is outside said body lumen. The invention includes at least one force and/or position sensor with a material in a generally stable temperature and austenite state, where the sensor is incorporated proximal to the catheter first end and an electrical resistance across the sensor changes according to a displacement of the catheter first end, where a measure of a force and/or a position on the catheter first end is attained.

In one aspect of the invention, the sensor is disposed to determine and map mechanical properties of patient tissue from the measure of the force and/or position data, where the sensor further includes a trigger element disposed to receive input from the sensor. Here, the trigger ceases the activity of the catheter when the sensor detects an excessive stress in the tissue mechanical properties.

In another aspect, the sensor is disposed to determine and map mechanical properties of patient tissue, where the properties are simulated in a virtual environment. In this embodiment, the sensor further includes a trigger element that is disposed to control activity of the catheter when the sensor detects an excessive stress or sudden reduction in stress in the tissue mechanical properties.

In another aspect of the invention, the sensor is disposed to detect force and/or position of the catheter, where the catheter is displaced by an actuator, and where the actuator can include a heated shape memory alloy or wire pulleys.

According to one embodiment of the invention, the sensor is formed from shape memory alloy (SMA).

In another embodiment, the sensor can be a compression spring, where the spring is disposed at the first catheter end and a resistance of the spring changes with strain, where the sensor detects axial forces at the first catheter end. According to this embodiment, at least one additional sensor is disposed along the spring, where the sensor is pre-strained and electrically isolated on at least one end, such that a position of the catheter first end and a compression force on the first tube end is attained from a deflection angle of the spring. In this embodiment, the sensor is laser-machined. According to this embodiment, the force information is relayed to a physician through a sensory method that includes electromechanical interface, haptic feedback, visual cues, visual renderings, or audible alerts.

In yet another aspect of the invention, multiple sensors are disposed along the catheter, where multiple displacements and multiple measurements exist, such that each displacement and each measurement is independent from other displacements and measurements.

In another aspect, the sensor is laser machined.

In one embodiment, the invention further includes an on-board integrated circuit, where the force and/or position on the catheter first end is interrogated. Here, the integrated circuit reads the sensors in an axial and/or a lateral sensing mode, where lateral and axial positions and/or forces are detected at the catheter first end.

In a further embodiment of the invention, at least one pair of the sensors is disposed in opposition, where the measurements are attained in at least two directions. Here, a first opposing sensor is compressed and a second opposing the sensor is stretched, where a linear response signal is attained from a difference of the resistances of the sensors.

In another embodiment, the sensor is made from a tube of SMA having a first tube end incorporated proximal to the catheter first end, and a second tube end incorporated along the catheter, where the sensor includes a first sensor end proximal to the first tube end and a second sensor end distal from the first tube end, where the sensor is laser machined. In this embodiment, at least one actuator is formed in the tube and includes a first actuator end proximal to the first tube end and a second actuator end distal from the first tube end, where the actuator displaces the first tube end from a central tube axis when heated, and a measure of lateral force on the catheter is attained when a change in resistance is measured across the sensor. In the current embodiment, the actuator shape includes a generally linear shape, zigzag shape, double zigzag shape, or curled flat winding shape. Additionally, the sensor element has a shape that can include a curved shape, a serpentine shape, a serpentine shape having vertical segments therein, a Greek-key shape, zigzag shape, double zigzag shape, and curled flat winding shape.

In another embodiment, the sensor is a torsion sensor, where the torsion sensor wraps around a circumference of the catheter, and a measure of a torque force on the catheter is attained.

In another embodiment, the sensor further includes a haptic physician interface, where the interface includes an external replica catheter of the catheter within a patient, such that the replica is manipulated by the physician to control the catheter within the patient and enabling the physician to feel forces being exerted by an environment around the catheter within the patient.

In yet another embodiment, a force and/or position sensor for active catheters includes at least one active interventional catheter having a first end and a second end, where the catheter first end is inserted to a body lumen, and the second end is outside the body lumen. The current embodiment further includes at least one force and/or position sensor, where the sensor includes a multi-core optical fiber having at least one Bragg grating along a length of the fiber. Here, the fiber cores are disposed off-center from a circular cross section of the catheter, where strains in the Bragg gratings are detected by a light source as the catheter is flexed, and a position of the sensor along the length is determined.

A further embodiment of the invention includes a position and force sensor for active catheters with a tube of the SMA having a first tube end, a second tube end and a tube center axis, where the second tube end is incorporated to a tip of an interventional catheter. In this embodiment at least one actuator is formed in the tube, where the actuator includes a first actuator end proximal to the first tube end and a second actuator end distal from the first tube end, at least one sensor formed in the tube, where the sensor is in a stable temperature and austenite state. The sensor includes a first sensor end proximal to the first tube end and a second sensor end distal from the first tube end, where the actuator displaces the first tube end from the axis when heated, where an electrical resistance across the sensor changes according to the displacement, and a measure of the position of the sensor and a measure of the force on the active catheter are attained according to the heating and the resistance. The current embodiment further includes a compression spring, where the spring is disposed at the first catheter end, and at least one the sensor is disposed along the spring, where the spring sensor is pre-strained and electrically isolated on at least one end, such that a position of the catheter first end and a compression force on the first tube end is attained. The current embodiment further includes a multi-core optical fiber having at least one Bragg grating along a length of the fiber, where the fiber cores are disposed off-center from a circular cross section, such that strains are detected in the Bragg gratings as the catheter is flexed and a position of the sensor along the length is determined. Additionally, a haptic physician interface is provided, where the interface includes an external replica catheter of the catheter within a patient, where the replica is manipulated by the physician to control the catheter within the patient and enables the physician to feel forces being exerted by an environment around the catheter within the patient.

BRIEF DESCRIPTION OF THE FIGURES

The objectives and advantages of the present invention will be understood by reading the following detailed description in conjunction with the drawing, in which.

DETAILED DESCRIPTION OF THE INVENTION

Although the following detailed description contains many specifics for the purposes of illustration, anyone of ordinary skill in the art will readily appreciate that many variations and alterations to the following exemplary details are within the scope of the invention. Accordingly, the following preferred embodiment of the invention is set forth without any loss of generality to, and without imposing limitations upon, the claimed invention.

This invention provides small position sensors for applications where localized sensing in a small volume of space is needed but where measurement of large relative displacement is also necessary. The invention addresses the need for a surgeon to be able to accurately position the tip of a catheter during minimally invasive therapy. The current invention further improves the quality of tactile feedback to a physician during catheter-based surgeries with an axial force sensor at the tip of the catheter that allows for the transmission of force information to the physician. One embodiment of this invention is a position sensor for active interventional catheters, where the sensor may be small and tube-shaped. Providing position feedback from a catheter during minimally invasive therapy allows for closed-loop control of the catheter tip position under computer-aided guidance and enable force feedback to the physician.

Shape memory alloys (SMAs), especially nickel-titanium (or nitinol), have become increasingly popular in many applications of robotics and medical devices. As actuators, they perform well in miniaturized applications because of their large power density. In addition, many passive devices take advantage of the material's superelastic properties.

Figure 1:
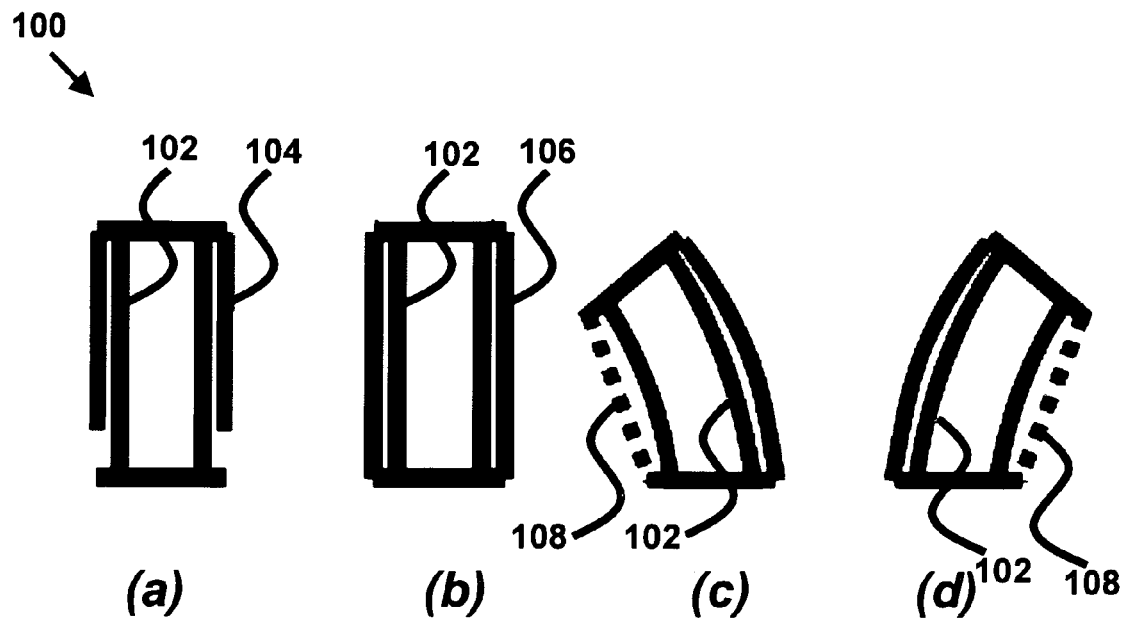
FIGS. 1(a)-1(d) show prior art diagrams of a SMA actuator-based-bending element for an active catheter.

SMA's undergo a solid phase transition between the stiff austenite phase and the more compliant martensite phase, induced by stress and temperature. After being plastically deformed in its low temperature martensite phase, the SMA material can recover strains up to 8% when heated to austenite. This is known as the shape memory effect and is used in temperature-dependent actuators. Additionally, a superelastic effect can be induced if the material is strained when its temperature is above its austenite finish temperature, $A_f$. In this mode, the material behaves elastically up to the yield stress, after which martensite crystals form and large material strains are achievable with little increased stress. FIGS. 1(a)-1(d) show diagrams of a prior art active catheter SMA actuator-based bending system 100. Shown in FIG. 1(a), a catheter 102 has SMA actuators 104 attached on opposing sides. FIG. 1(b) shows the configuration of FIG. 1(a), with the actuators shown as pre-strained actuators 106, where they have been stretched along the length of the catheter 102. FIGS. 1(c) and 1(d) show the effect of how a heated actuator 108 returns to its original length, causing the catheter 102 to bend and thus "steering" the catheter 102.

Figure 2:
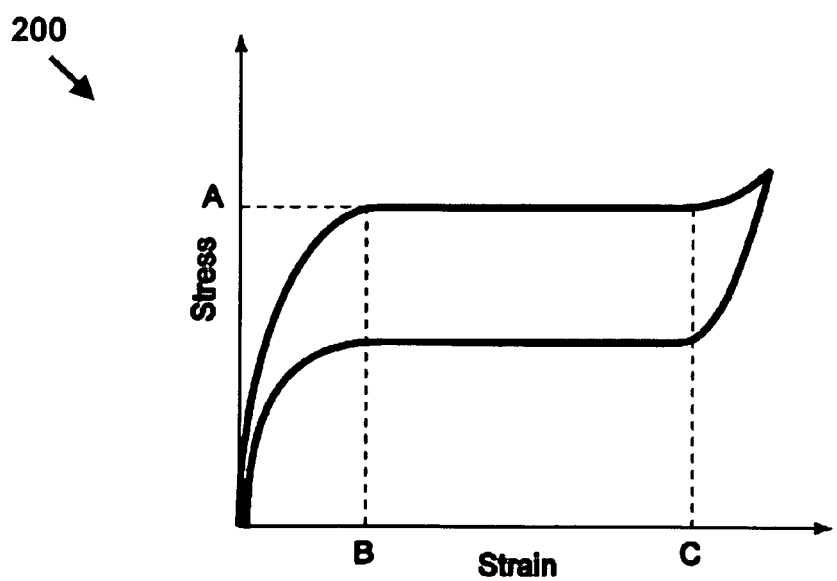
FIG. 2 shows a typical stress strain curve for shape memory alloy initially in austenite phase.

In addition, if $A_f$ is set below the operating temperature (e.g. room temperature), the material will exhibit a superelastic behavior when deformed, such that martensite is stress-induced and large strains are possible with little permanent deformation. FIG. 2 shows a typical stress strain curve for shape memory alloy initially in austenite phase. As shown, points A and B correspond to the yield stress and strain, respectively. There is a stress plateau between points B and C, resulting in a "superelastic" effect.

Figure 3:
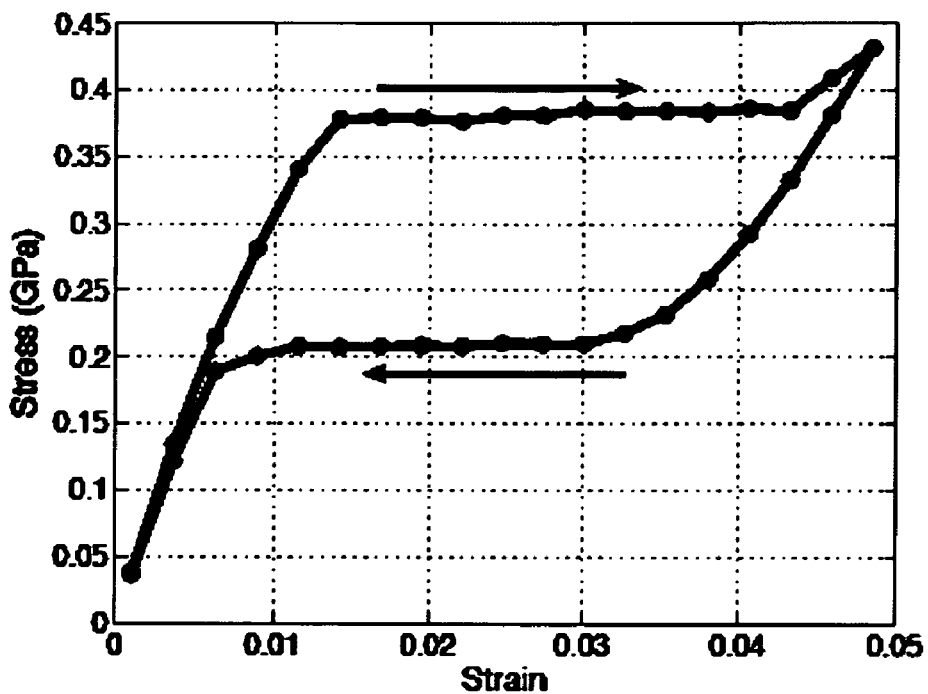
FIGS. 3(a)-3(b) show a prior art superelastic stress-strain curve of a SMA strip cut from nitinol tubing, and a prior art relative resistivity vs. strain, showing quadratic and linear regions, respectively.
Figure 3:
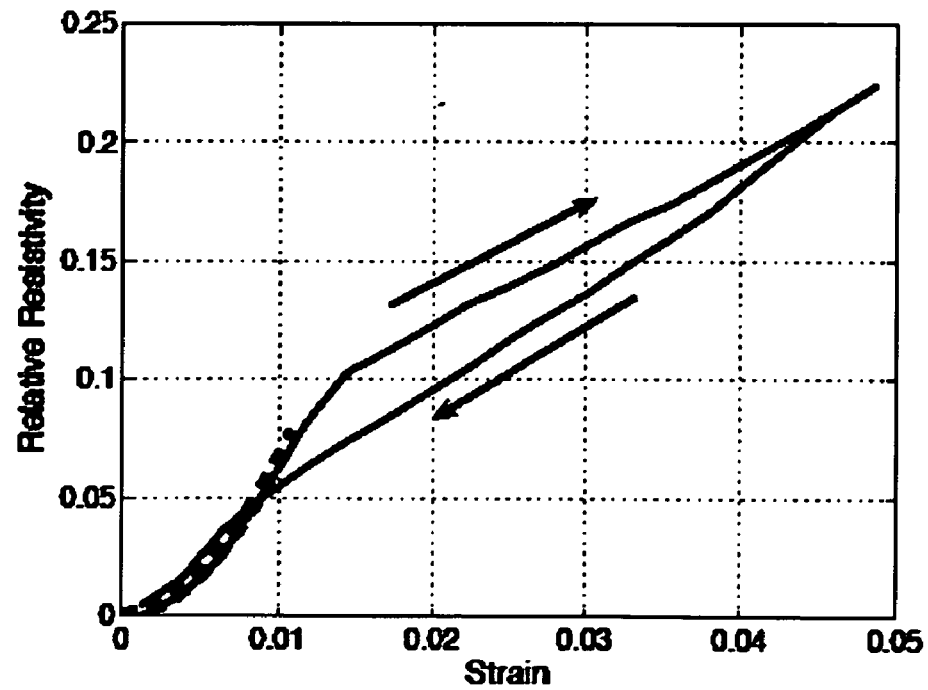

FIGS. 3(a) and 3(b) show the stress-strain relationship of an 11.4 mm long, 127 μm wide strip cut from nitinol tubing, exhibiting the typical "flag-shaped" superelastic hysteresis response. Both nitinol wires and strips of nitinol tubing exhibit a non-hysteretic quadratic resistivity with strain up to the yield stress, after which the resistivity increases linearly but has hysteresis. FIG. 3(b) shows the relative resistivity vs. strain with quadratic and linear regions. As can be seen in the figure, the resistivity can increase up to 10% before the yield stress when axially strained. If stresses in the material are kept below or near the yield stress, the resistivity of the SMA should not exhibit hysteresis. Shown as the dashed line in FIG. 3(b), an experimental fit to the axial strain data suffices to produce a quadratic model that is useful for comparison and relatively quick finite element analysis (FEA) of more complex structures.

The geometric design of the SMA sensor is constrained by a number of factors, including the anatomy of the human body, the capabilities of the laser-machining process, and integration with an SMA actuator or wire-pulley actuator onto an active catheter. In addition, the mechanical and electrical properties of the sensor are interdependent and reliant on the dimensions of the sensor.

For intracardiac procedures, the size of an active catheter is limited to 2-3 mm diameter in order to fit within the blood vessels. For example, the catheter may need to travel into the left atrium of the heart, which can be approximated as an ellipsoid with a minor axis of 3-4.5 cm and a major axis of 4.5-7 cm. This restricts the bend diameter of the catheter to approximately 2.5 cm. To achieve this bend diameter with 8-10 bending segments on the catheter, SMA actuators are nominally 1.5 mm long and cut from 1 mm diameter tubing. They are designed to be prestretched to 300 μm elongation and to operate in the range of 150-450 μm elongation without significant fatigue.

The sensors of the current invention accommodate this length and prestretch. In addition, the sensors are compliant compared to the SMA actuators and wire-pulley actuators, for example where the actuators have an austenite stiffness of 150 mN over 300 μm elongation, or roughly 3.8 mN/μm, the sensors have a stiffness of 150 mN over 300 μm, or roughly 0.5 mN/μm. The current invention uses the laser-machining process, which provides feature sizes down to 25 μm. In one aspect, to ensure accuracy in cutting, strut widths are kept above 40 μm. The tubing and strut thickness can also be controlled by electropolishing, which isotropically removes material and smooths the surface to improve fatigue life. Electropolishing also removes the effects of laser-heating along the cut edges, although this heat affected zone (HAZ) is typically very small for this process.

As shown in FIG. 3(b), shape memory alloys in the superelastic phase exhibit a non-hysteretic quadratic resistance behavior below a given strain. By using the laser-machining process to design different shapes and create compliant structures, on embodiment of the current invention takes advantage of this behavior to create a resistance-based sensor from SMA tubing. By developing a sensor with a shape factor similar to that of the SMA actuators and the catheter itself, a number of sensors can be distributed along the length of a catheter to detect the catheter's deformation when actuated.

According to the current embodiment, the distributed position feedback systems for interventional catheters includes a catheter with maneuverable tip, a distributed position feedback system over at least part of the catheter, and a mechanical or virtual representation of the position feedback information. In one aspect, the distributed feedback system can be an optical sensing system, where the optical feedback system relies on fiber optic sensors with multiple Bragg gratings to detect bending in many directions. In a further aspect, the mechanical system can be enabled by a scaled-duplicate of the actual active portion of the catheter. A mechanical/virtual representation can be in the form of a virtual haptic interface, where the virtual representation can entirely reside in a 3D virtual environment, or the virtual representation can entirely reside in a 3D virtual environment where other devices are also represented and simulated. Alternatively, the virtual representation can entirely reside in a 3D virtual environment where the patient environment (e.g. vascular space) is also represented and updated either in real-time or as an imported structure. Further, the mechanical properties of the patient tissue can be inferred from the positional data and simulated.

In another aspect of the current embodiment, more than one catheter is represented, where two or more catheters have coordinated activities. Additionally, one of the catheters may have additional imaging capabilities, where the plane of the imaging catheter can be projected in the mechanical or virtual environment.

According to another embodiment of the current invention, a tube-shaped position sensor is provided for applications where localized sensing in a small volume of space is needed and where measurement of large relative displacement is also necessary. In one aspect, design flexibility is afforded by laser-machining of nitinol tubing with the electrical resistance characteristics of nitinol material to create a functional large displacement, small volume position sensor.

Shape memory alloys (SMA), the most common of which are made from Nickel Titanium (or nitinol), are known for their impressive mechanical properties, especially the ability to be deformed at large strains without permanent plastic deformation. However, these materials exhibit a large mechanical hysteresis when deformed beyond the yield stress. Further, the electrical resistance of the material also exhibits hysteresis beyond the yield stress. However, nitinol has some useful electrical properties at low strains. For example, at room temperatures, SMA materials in austenite phase have an electrical resistance that increases quadratically with strain up until the yield stress. Furthermore, the resistance-strain curve does not have hysteresis below about 1.2% strain. According to one aspect of the invention, these material properties function as a useful strain sensor below that strain value.

In one aspect of the invention, laser-machining of SMA tubing enables tailoring the mechanical characteristics of a SMA structure without sacrificing volume, shape factor, or fatigue life. For example, in a catheter application, winding shapes can be provided that fit in a tubular shape, have the large displacement characteristics needed to measure the bend of the catheter, yet do not present significant mechanical resistance to the catheter bending. Such an SMA structure can be cut from tubing or a sheet to create a sensor to the form factor of a desired device. In one aspect, finite element analysis (FEA) can be used to analyze and design the mechanical structure. For example, in a catheter application a support structure can be cut out of tubing to incorporate at least one SMA sensor as part of the structure. According to one aspect, one end of the SMA sensor could be detached from the structure and reattached so that it is electrically insulated from the support structure. Further, lead wires can then be attached to the two ends of the SMA sensor to measure its resistance.

According to one embodiment of the invention, when a SMA sensor is attached to a catheter, the catheter can be bent so that the sensor stretches and its resistance changes. Measuring this resistance will then yield information about the bending angle. With multiple sensors distributed along the length of the catheter, more information can be obtained about the bending angle of the catheter. In addition, sensors can be placed orthogonally so that multiple planes of bending can be measured. Furthermore, if the sensors are placed antagonistically so that the catheter bending stretches one sensor while compressing the other, taking the difference between the two sensors will cancel the quadratic component and linearize the overall sensor output. This differential configuration also has the effect of canceling out fluctuations due to temperature changes.

According to one embodiment of the invention, a SMA-based sensor is laser-machined from Nickel Titanium tubing that is austenitic at room temperature. A simplified Finite Element Analysis (FEA) is used with material properties based on experimental testing to design the mechanical and electrical properties of the sensor structure and achieve the desired characteristics. Through a rapid prototyping process of FEA, laser-machining, and experimental verification, multiple iterations of the sensor design are quickly achieved.

Figure 4:
FIG. 4 shows a photograph of two strips of laser-machined 127 μm SMA tubing, showing the edge of an American nickel for scale, according to the current invention.

To demonstrate the feasibility of using a resistance-based SMA sensor, the mechanical and electrical properties of nitinol tubing were tested with characteristics listed in Table 1. A 127 μm wide strip of laser-machined SMA tubing was initially characterized and its stress-strain characteristics were compared to those of an SMA wire of similar cross sectional area. Due to the need to stabilize the piece during the laser-machining process, the SMA strip was furnished with support tabs along its length, as shown in FIG. 4.

TABLE 1

| Nitinol tubing characteristics. | |
|---|---|
| Outer Diameter | 1.09 mm |
| Wall Thickness | 127 μm |
| $A_f$ | <15° C. |

Figure 5:
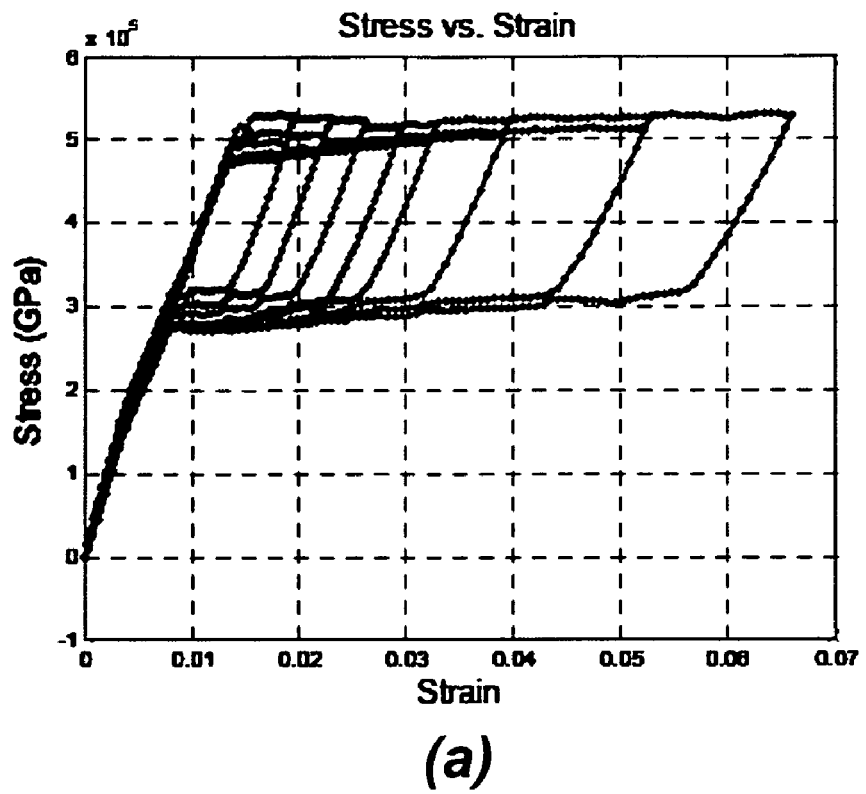
FIGS. 5(a)-5(b) show stress-strain data and resistivity-strain data from varying extensions of a piece of 30.3 mm, 127 μm diameter nitinol wire, respectively, according to the current invention.
Figure 5:
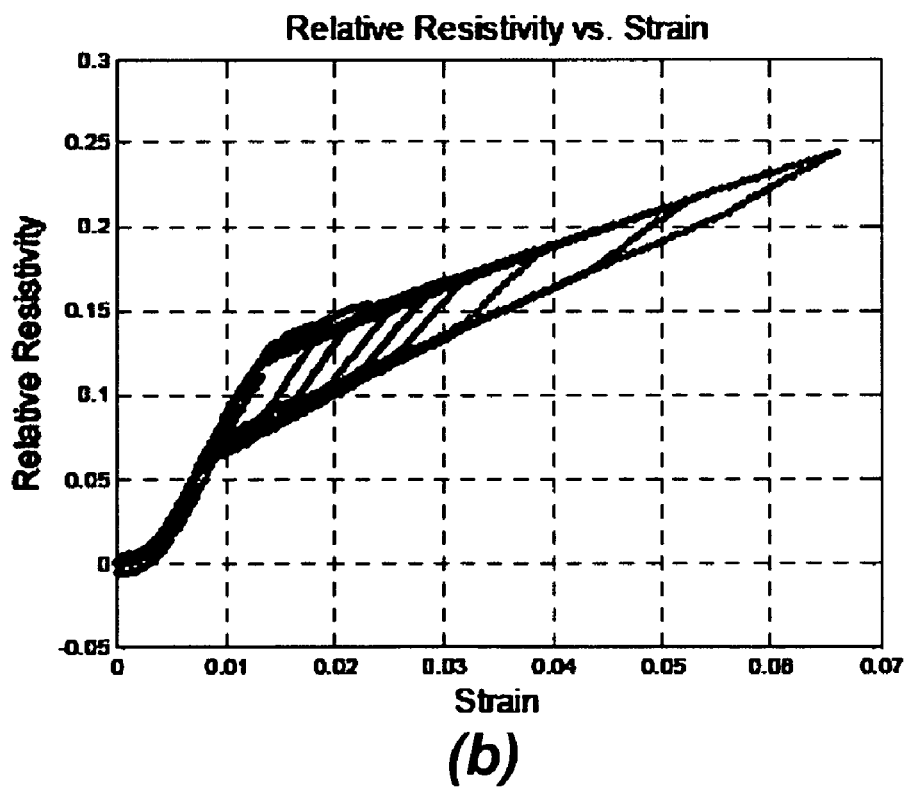

FIGS. 5(a) and 5(b) show stress-strain data from varying extensions of a piece of 30.3 mm, 127 μm diameter nitinol wire, where FIG. 5(a) shows a stress vs. strain relationship for a SMA wire, and FIG. 5(b) shows a relative resistivity vs. strain of a SMA wire. The wire exhibits a stress plateau at ~470 MPa. The resistivity vs. strain characteristic of the wire in FIG. 5(b) shows that in the region below 1.2% strain, the response is roughly quadratic, but above that value it takes on a linear but hysteretic shape. This simple exemplary model assumes constant volume to calculate the resistivity, but this is likely not valid for higher strain values. Beyond the yield stress martensite is induced in the material, which can have many crystal variants and hence a more complicated resistivity response.

FIGS. 6(a) and 6(b) show the response from the 127 μm wide strip of SMA tubing, where FIG. 6(a) shows a stress vs. strain relationship for a strip cut from SMA tubing, and FIG. 6(b) shows the relative resistivity vs. strain of a SMA tube strip. This, along with manufacturing differences in the tube material as compared to the wire, may account for the irregularities in the tube strip discontinuities. The overall shape of the response, however, is similar to that of the wire with 350 MPa yield stress at approximately 1.2% strain. This value correlates well with the manufacturer's data for yield stress from the tubing, 380 MPa. Furthermore, the shape of the relative resistivity vs. strain characteristic, shown in FIG. 6(b), matches that of the wire very closely.

According to the von Mises criterion, the yield stress in a given piece of material will be less than or equal to the yield stress in the same material under tensile test. That is, by determining the stress-strain characteristics of the nitinol tubing under tensile test, one should be able to determine the maximum von Mises yield stress for the material in other configurations besides axial strain. That information can then be used in the material model for simulation of the current invention.

Using the mechanical and electrical data from the tube strip, a simple exemplary FEA material model was developed. The simulation uses a perfectly plastic material with yield stress of 350 MPa. The elastic modulus for the linear portion of the model is calculated from the yield stress and yield strain from the tube strip tests. The material properties for simulation are listed in Table 2.

TABLE 2

Austenite Material Parameters for FEA Simulations.

| Property | Simulation | Source |
| --- | --- | --- |
| Stress Plateau | 350 MPa | Experiment |
| Elastic modulus | 28 GPa | Experiment |
| Resistivity | 82 µΩ-cm | Manufacturer |
| Poisson's Ratio | .33 | Literature |
| Density | 6450 g/cm$^3$ | Literature |

Critical values are taken from experiment and others are taken from the manufacturer or general literature.

The measured elastic modulus seems significantly lower than the manufacturer's values of 41-70 GPa, however the measured value has been used in simulations with reasonable results. The primary purpose of this model is for information in the design of the SMA sensor geometries and to allow comparison among different finite element designs, however, but not necessarily to obtain a perfect prediction of the sensor behavior.

Using a least-squares fit of the relative resistivity vs. strain data from the tube strip, the inventors modeled the quadratic stress-dependent resistivity for the SMA sensor structure. The resistivity is given by the following expression:

$$\rho = \rho_0(1 + A(s/E)^2 + B(s/E) + C)$$

where $\rho_0$ is the resistivity given by the tubing manufacturer, E is the elastic modulus of the nitinol in the linear region of the stress-strain curve, s is the von Mises stress component at a given point, and A, B, and C are empirically determined constants.

This current model assumes that the resistivity will reach a constant maximum value at the yield stress and does not account for any changes in resistivity beyond the yield stress.

Initial design considerations of the current invention were to develop structures that would be mechanically compliant relative to the SMA actuators, but also would achieve large changes in resistance value. To achieve the former, the inventors developed thin structures with 30 um features, since a smaller cross-sectional area decreases the stiffness of the device. In addition, a flat-spring geometry was used to tailor the overall mechanical stiffness.

To achieve larger resistance changes, design structures that would undergo a more homogeneous stress profile have been provided. Using curved winding structures aids in this goal, but it is challenging to achieve a homogeneous stress profile, since winding structures are inherently prone to stress concentrations. In addition, tensile and compressive stresses on either side of the struts tend to counteract each other to reduce the overall resistance change.

Figure 7:
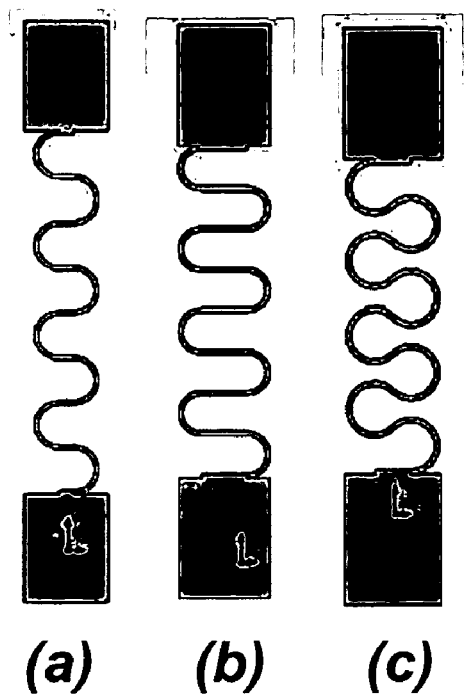
FIGS. 7(a)-7(f) show CAD drawings and photographs of shape memory alloy sensor designs, according to the current invention.
Figure 7:
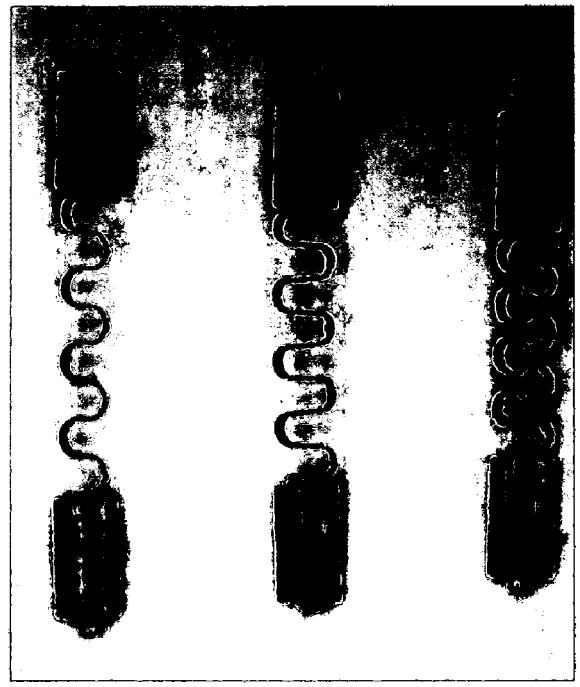
Figure 8:
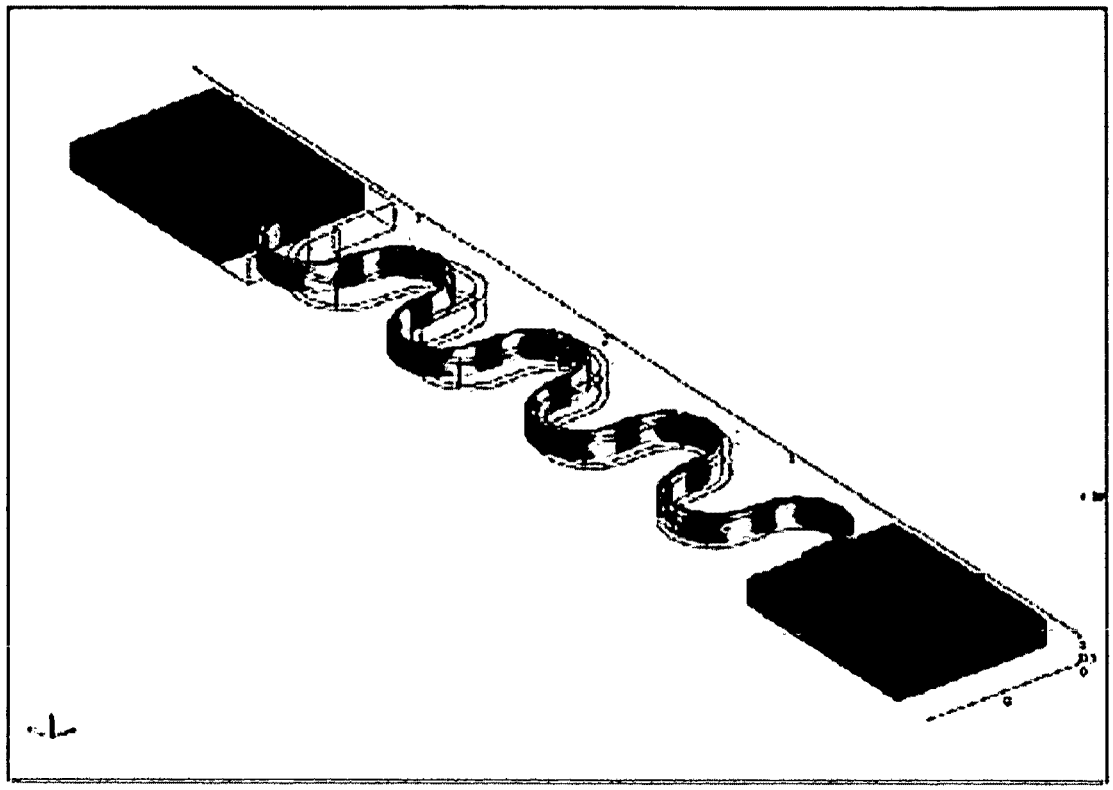
FIG. 8 shows finite element analysis results for SMA sensor Design 1 of FIG. 7, according to the current invention.

Three exemplary sensor designs are made available to demonstrate the efficacy of using SMA structures as position sensors. These structures are shown in FIGS. 7(a)-7(f), where FIGS. 7(a)-7(c) show CAD drawings of shape memory alloy sensor designs and FIGS. 7(d)-7(f) show photographs of the three sensor designs, respectively. Using the above material parameters, each of these sensor structures were simulated using FEA to determine the resistance and stress profiles throughout the structure. An example of the FEA results for Design 1 of FIG. 7(a) is shown in FIG. 8.

Figure 9:
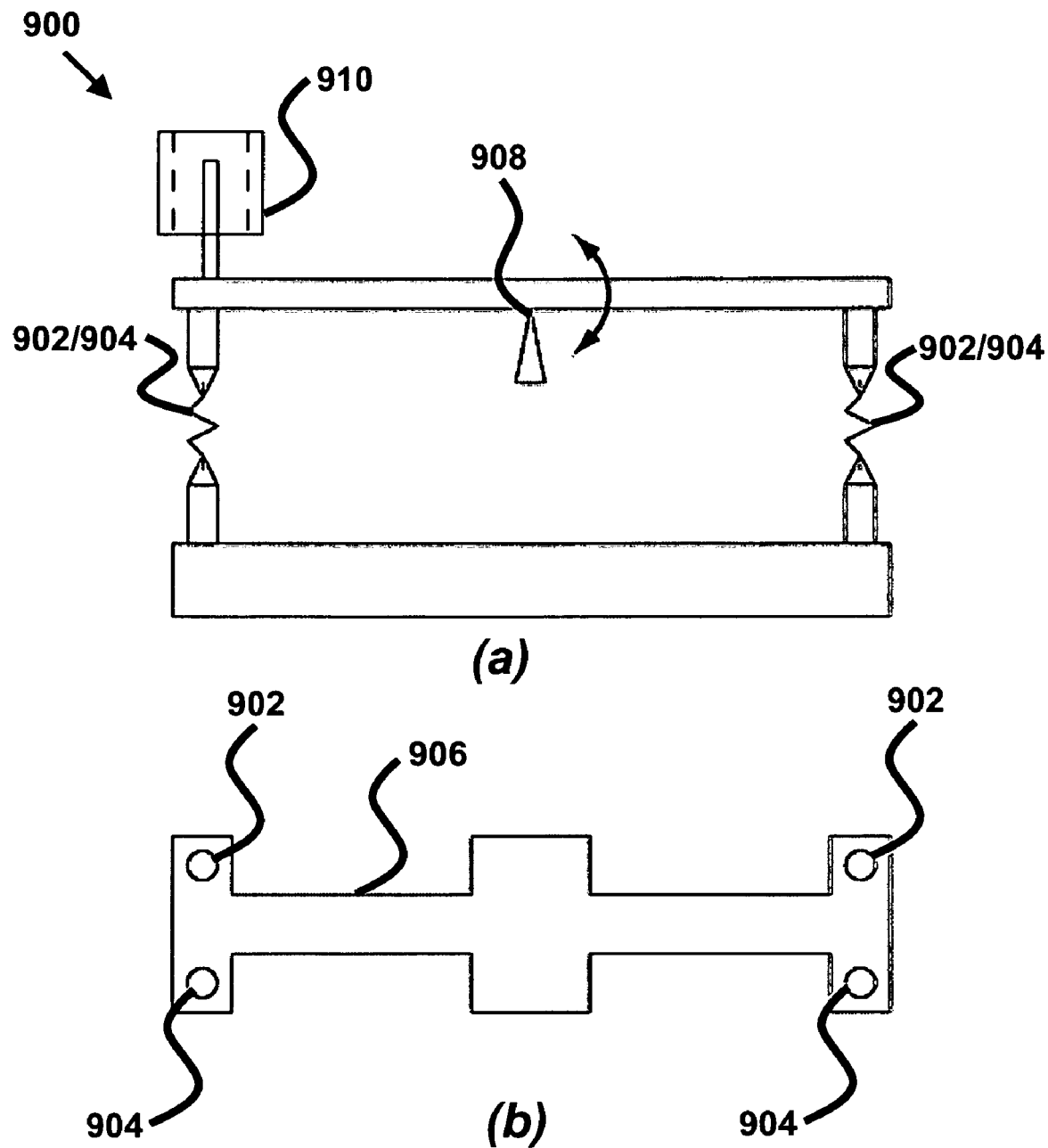
FIGS. 9(a)-9(b) show side and top views, respectively, of a schematic drawing of a dynamic setup for active actuator and sensor testing, according to the current invention.

Both the static and dynamic characteristics of the SMA sensor structures were verified. A dynamic setup 900 shown in FIG. 9 allows for mounting of two SMA actuators 902 and two SMA sensors 904 in antagonistic configuration, where FIG. 9(a) is a side view of the dynamic setup 900, and 9(b) is a top view of the dynamic setup 900. Two sensors 904 and two actuators 902 are attached to either side of a central beam 906, which pivots on a knife edge 908. The core of a linear variable differential transducer (LVDT) position sensor 910 is attached to the left side of the beam 906 and moves vertically within the housing (not shown), without contacting it, as the beam 906 deflects. This setup ensures that minimal friction and stiction are introduced into the verification. Because the actuators are small in length relative to the beam, the small angle approximation is assumed valid and lateral motion of the actuators 902 and sensors 904 is minimal.

The quasi-static setup was used to measure the force-elongation and resistance-elongation characteristics of the different sensor designs. Although the sensor designs were of different lengths, they were tested in terms of percent-elongation of total length. Because the actuator is nominally prestrained at 20% elongation in normal operation, the SMA sensors were tested at this elongation as well.

Figure 10:
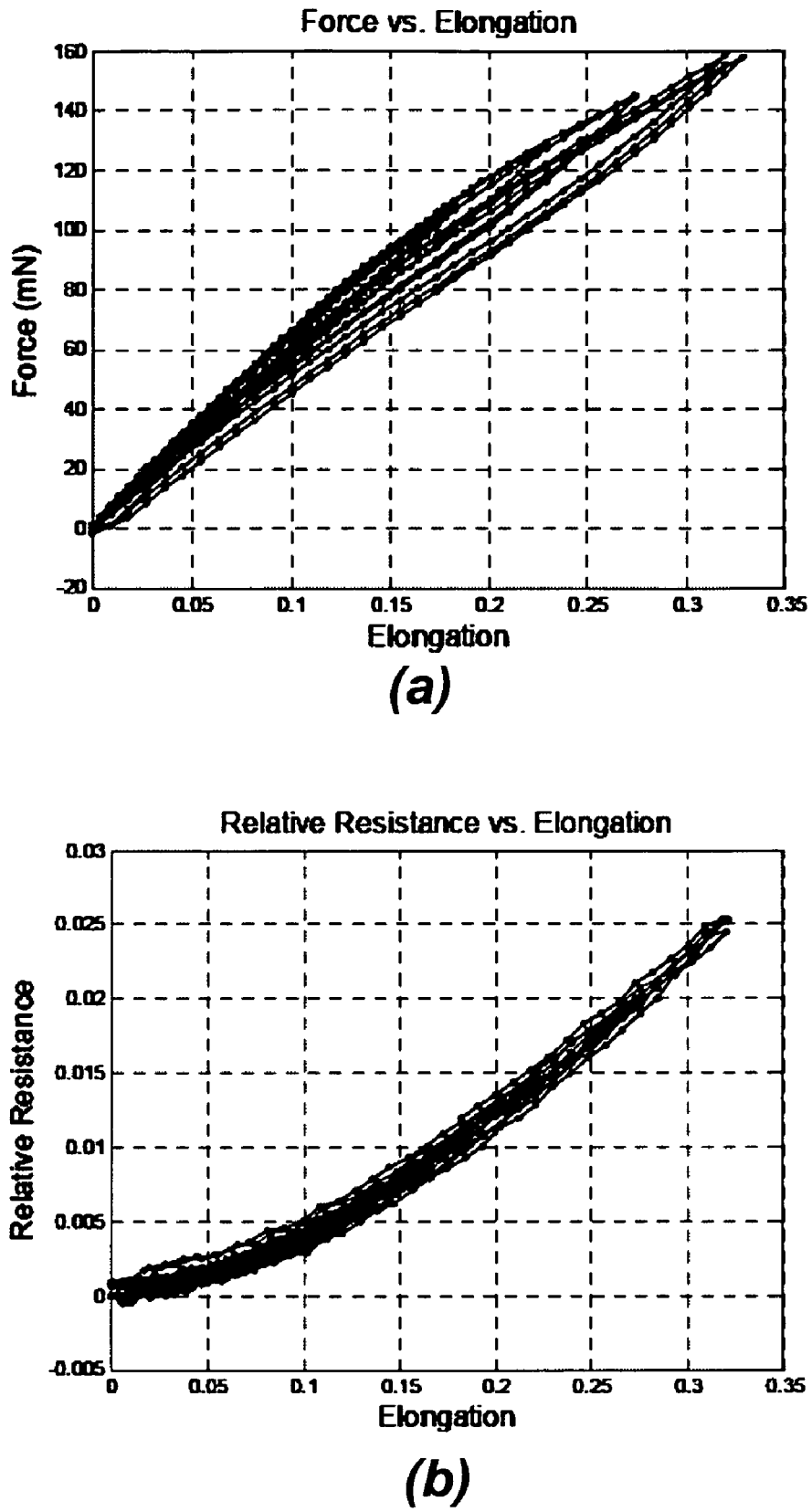
FIGS. 10(a)-10(b) show results of these tests for sensor Design 2 of FIG. 6(b), for varying elongations, according to the current invention.

FIGS. 10(a) and 10(b) show the results of these tests for sensor Design 2 of FIG. 6(b) for varying elongations. At 20% elongation, the force is about 120 mN, yielding an estimated linear stiffness of 274 N/m. The force-elongation curves exhibit some amount of hysteresis, indicating that portions of the sensor are reaching the yield stress and martensite is being stress-induced in the structure. The actuators used have roughly 6600 N/m stiffness in austenite phase, and these sensors exhibit less than 5% of this value. The invention includes further refinement and optimization of the design, so they are made even more compliant.

The resistance response of the sensor structure exhibits the quadratic behavior expected from the preliminary material characterizations. Although a given geometry cannot achieve the same resistance change as an axially strained strip, it should be apparent that structures can be provided to undergo larger resistance changes than the current sensor geometries demonstrated in this example.

Table 3 shows some key response data from the three different sensor designs. Resistance is measured at 0% elongation, and all other values are measured at 20% elongation. The stiffness is calculated as an approximation using the force and displacement values at 20% elongation. Although the resistance change in the three designs is similar in magnitude, Design 2 had the best performance over multiple cycles at 30% elongation. That is, the overall resistance change does not necessarily give indication of which design has higher stress concentrations throughout the structure. It should be apparent that many designs can be implemented to address stress concentrations in the sensors of the current invention.

TABLE 3

Response data for three sensor designs.

| Attribute | Design 1 | Design 2 | Design 3 |
| --- | --- | --- | --- |
| Length of active portion | 2.67 mm | 2.19 mm | 1.83 mm |
| Resistance (Ω) | 1.18 Ω | 1.31 Ω | 1.35 Ω |
| Maximum ΔR | .025 Ω | .031 Ω | .032 Ω |
| Max Relative ΔR | 1.2% | 1.25% | 1% |
| Stiffness | 337 N/m | 274 N/m | 273 N/m |

Values are listed for 20% elongation of the sensor.

The quadratic resistance response for the sensor exhibits a relatively linear region above 10-12% elongation. Given that the SMA actuator is designed for actuation between about 10 and 30% elongation, operating in this region can supply sufficiently linear output for a sensor. It is preferable, however, to employ methods of ensuring a linear output.

Figure 6:
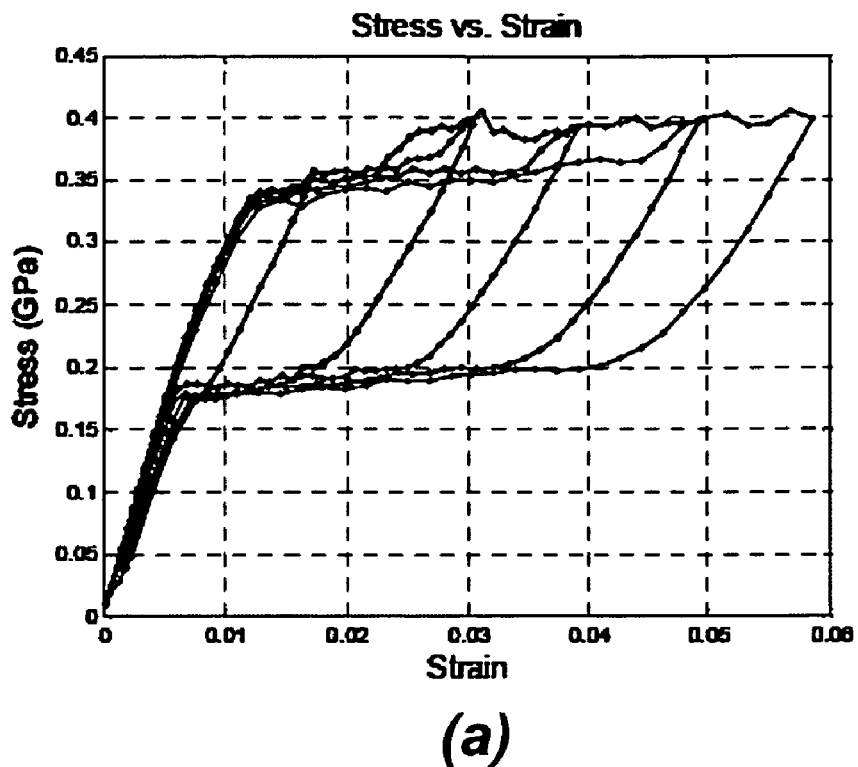
FIGS. 6(a)-6(b) show stress-strain data and resistivity-strain data from a 127 μm wide strip of SMA tubing, respectively, according to the current invention.
Figure 6:
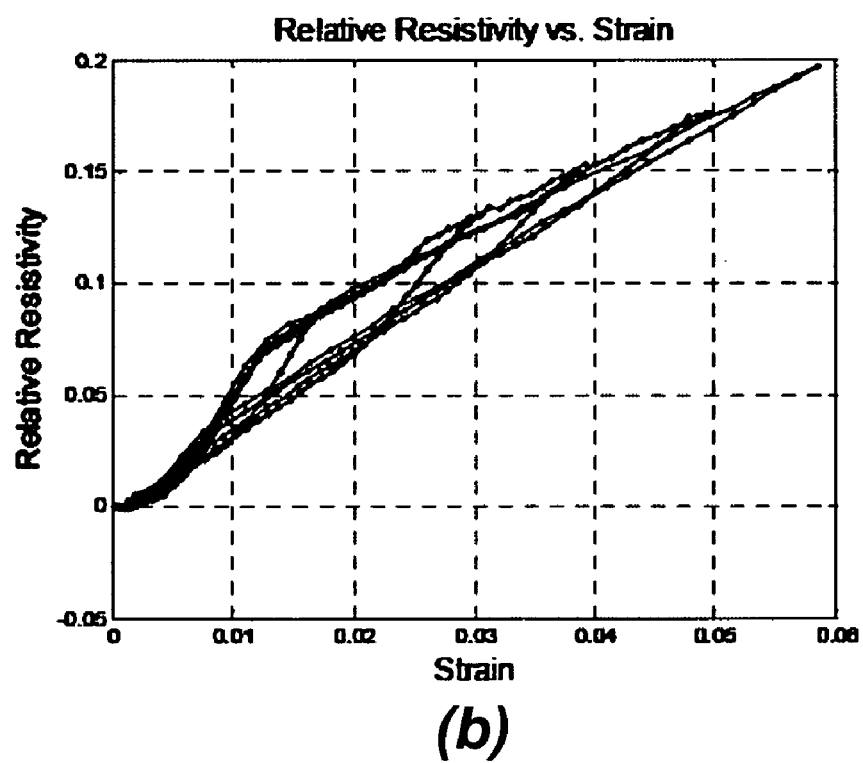
Figure 11:
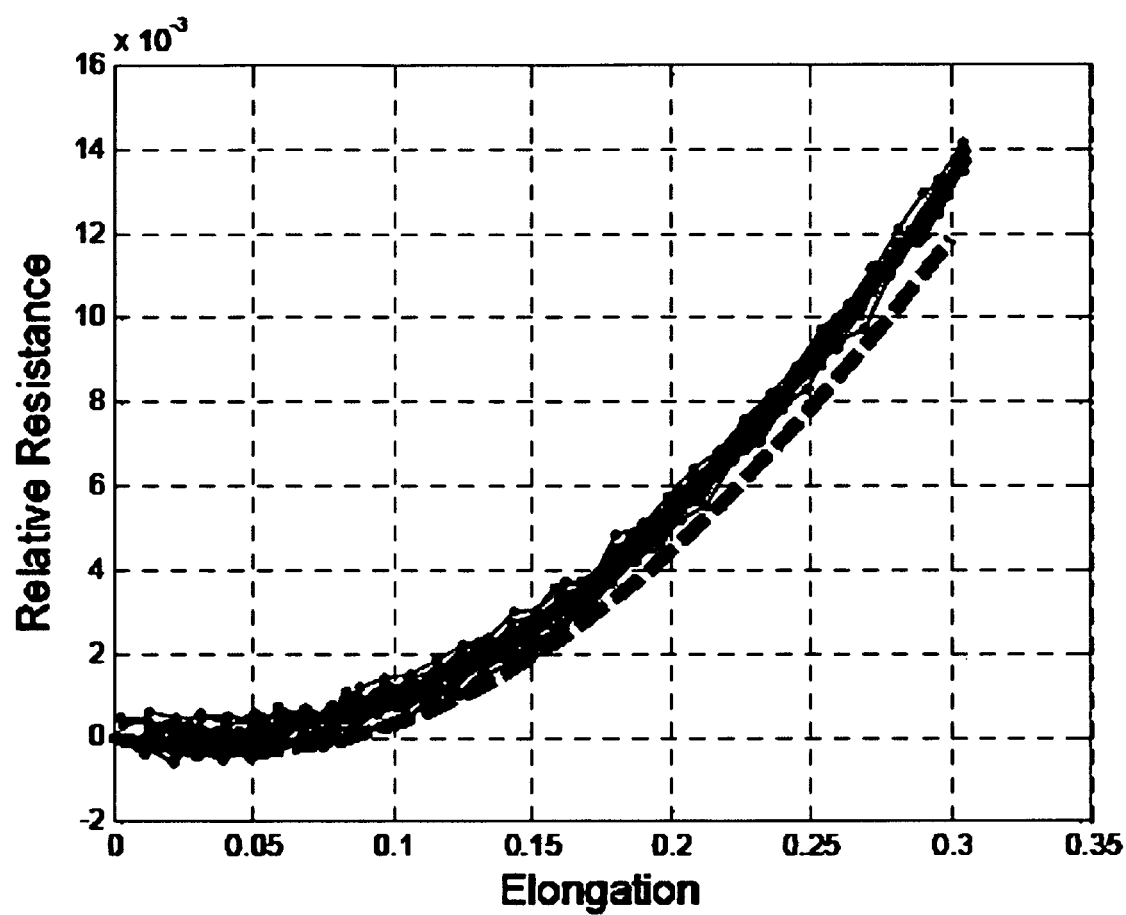
FIG. 11 shows relative resistance vs. elongation for varying elongations of sensor Design 2 of FIG. 6(b) including a quadratic-fit line (dotted), according to the current invention.

To verify the FEA model, a comparison is made of the relative resistance of sensor Design 2 of FIG. 6(*b*) to the output from the model, which is based on experimental testing of the SMA tube strips. FIG. 11 shows good agreement between the FEA simulation results and the results from the sensor. There can be some variation in the model results due to variations in the initial material characterizations, but the model generally does well to roughly predict the behavior of the sensor.

Figure 12:
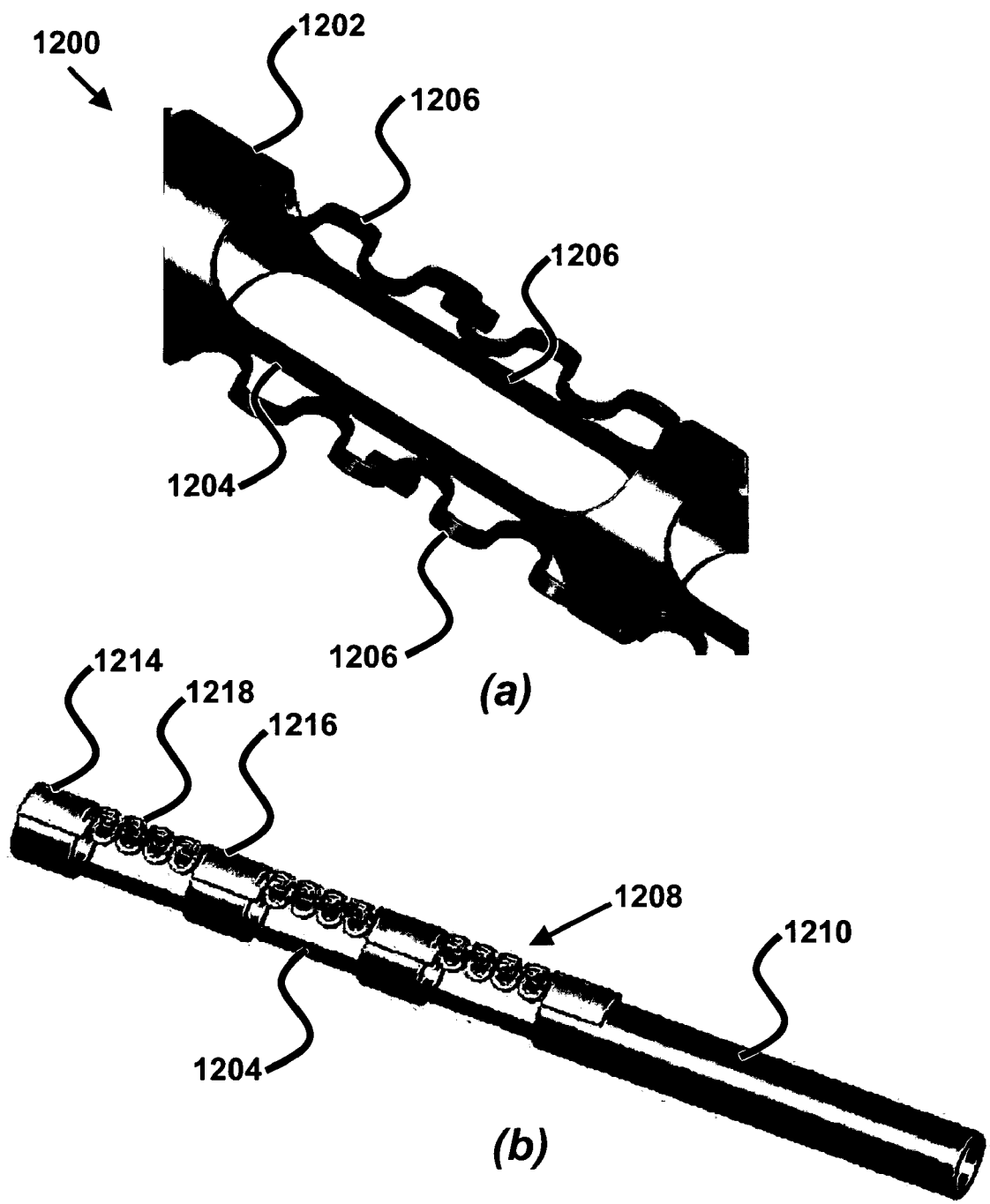
FIG. 12(a)-12(c) show perspective views of a differential configuration of a SMA tube, attachable SMA sensors mounted on SMA backbone used as an active catheter, and actual attachable SMA sensors respectively, according to the current invention.
Figure 12:
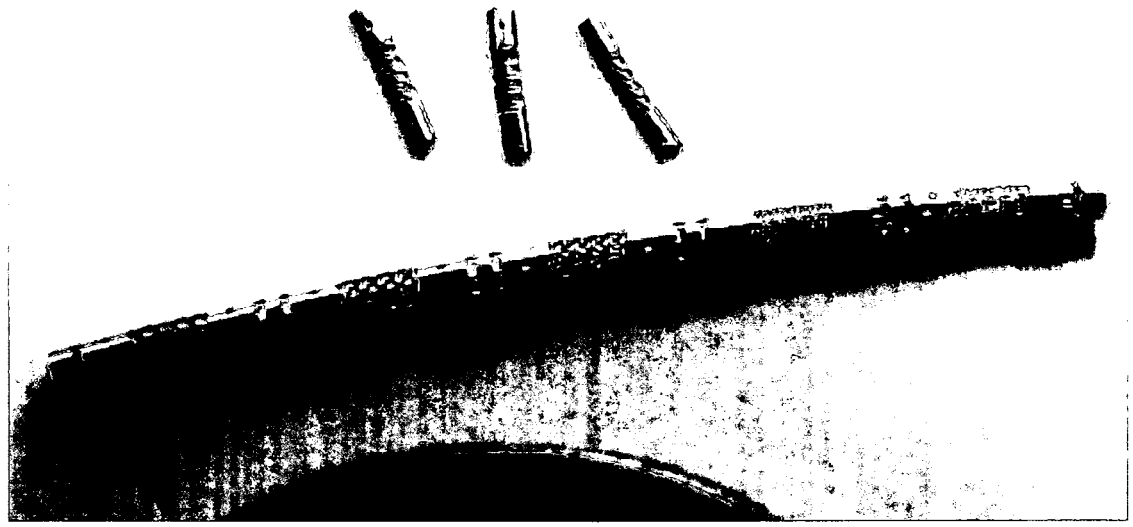

According to one embodiment of the invention, two SMA sensors can be arranged in a differential configuration to create a linear output. FIG. 12(*a*) shows a perspective view of a differential configuration 1200 of a SMA tube 1202 having an opposing pair of actuators 1204 and two opposing sensors 1206. The sensors 1206 can be mounted on opposite sides of the bending segments 1204 (not shown), where both sensors 1206 are prestrain by the same amount. Because the sensors 1206 can be laser-machine with high precision, both sensors 1206 will have roughly the same quadratic response. When the sensors 1206 are mounted on opposite sides of the bending segments 1204 (not shown), the bending segment 1204 flexes in one direction, one sensor 1206 will be stretched while the other will be compressed. In this antagonistic configuration, one sensor 1206 will have the following resistance:

$$R_1 = A(x-x_0)^2 + B(x-x_0) + C,$$

whereas the other sensor will have the resistance characteristic, $$R_2 = A(x-x_0)^2 - B(x-x_0) + C$$

where $R_1$ and $R_2$ are the resistances of the two sensors, A, B, and C are constants, x is the elongation, and $x_0$ is the prestrain value. If the difference between the two $R_1-R_2$ are taken, a linear output is obtained:

$$R_1 - R_2 = 2B(x-x_0)$$

According to one embodiment of the invention, the position-sensing device can be incorporated to the active region of a catheter, to provide feedback of the position of the portion of the catheter nearest the tip. The active region of the catheter is the region designed to be motive relative to a certain reference point near the tip. For example, in ablation procedures for atrial fibrillation, the reference point may be the interatrial septum, and the active region of the catheter maybe the portion that extends from the septum into the left atrium during the procedure. Depending on the particular surgery, this active region may vary in length, but in general it may be on the order of 4-6 cm. FIG. 12(*b*) shows a perspective view of a series attachable SMA sensors 1208 mounted on SMA backbone 1210 used as an active catheter, where the backbone 1210 has integrated actuators along its length (not shown). As shown, the attachable SMA sensor 1208 includes a first attachment end 1214, a second attachment end 1216, and a compliant middle portion 1218, where the attachment ends 1214/1216 can have electrodes or wiring at their respective ends (not shown) to measure a change in resistance as the compliant middle portion 1218 stretches or compresses due to movement from the actuators (not shown). FIG. 12(*c*) shows a photograph of actual attachable SMA sensors 1208 that are fabricated from SMA tubing, where shown are sensors, both as they are cut and polished on the tubing and after being released from the tubing. The edge of an American penny is shown for scale.

The exemplary sensors shown in FIG. 12(*c*) were electropolished 10 μm per side, or 20 μm total. To achieve a measurable absolute resistance in a short overall length, the sensor includes a winding structure, according to one embodiment. Compared to the axial strain case, this limits the amount of resistance change achievable, since the stresses will not be uniform over the structure, and peak stresses must be kept below the yield stress to avoid hysteresis in the resistance response. Curved and rounded turns can aid in reducing stress concentrations, but the overall change in resistance is significantly less than in the axial case. The stiffness of the sensor also depends on a chosen geometry and dimensions. In general for winding shapes, longer, wider, and thinner structures will tend to be less stiff. For a given tube thickness, more compliant structures tend to have lower induced strains and hence will have lower change in resistance. Selection of thinner tubing or more electropolishing removal can decrease the stiffness while increasing the resistance and signal output achievable.

Figure 13:
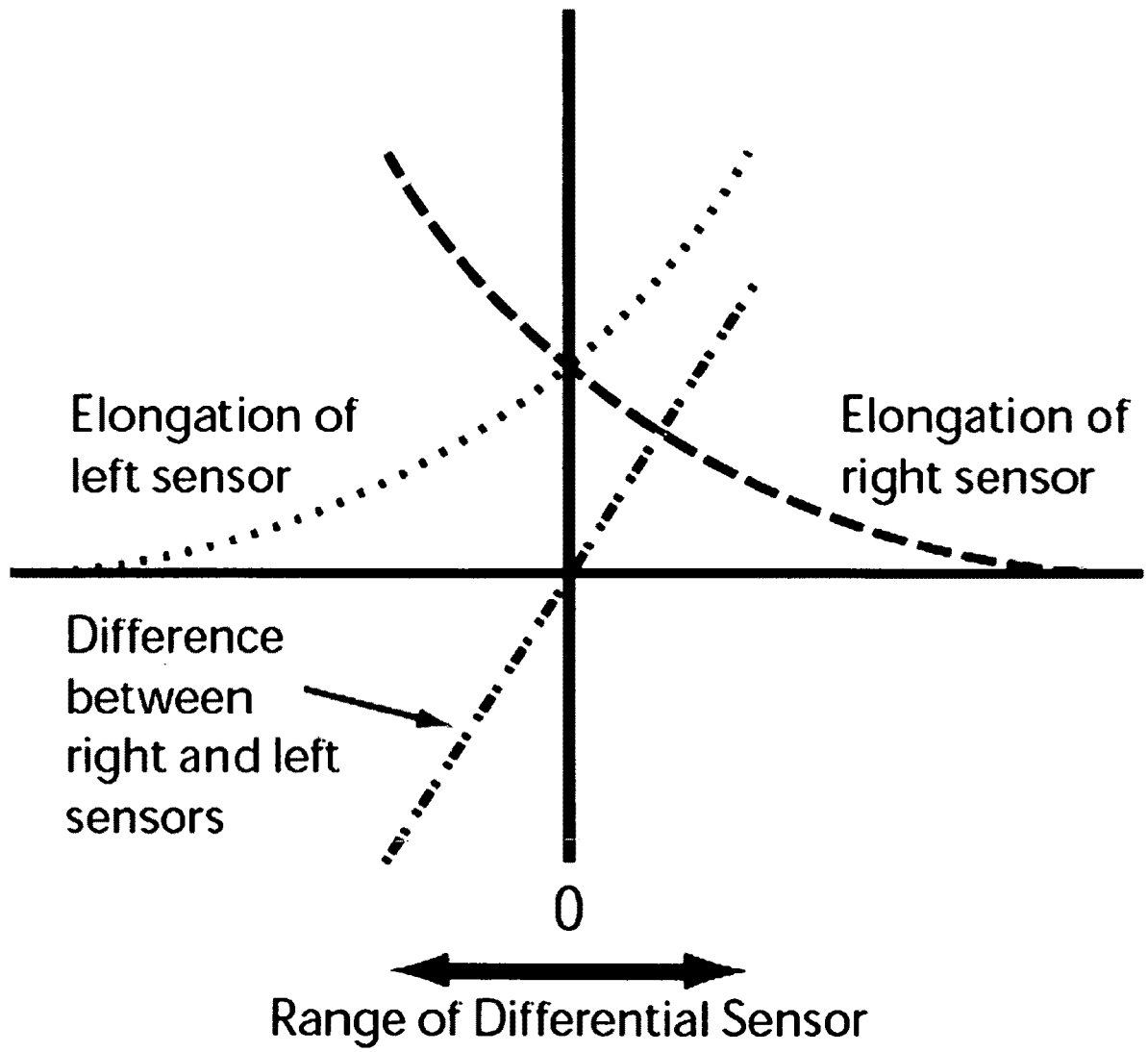
FIG. 13 shows a theoretical resistance of the two sensors and the effect of taking the difference of their responses, according to the current invention.

FIG. 13 illustrates the theoretical resistance of the two sensors and the effect of taking the difference of their responses. The gray area represents the useable range of the differential sensor.

To demonstrate this, one sensor 904 was connected on each side of the beam 906 in the dynamic testing setup 900 of FIG. 9 and a micropositioner (not shown) was moved up and down on the right side with the left side counterweighted (not shown). This effectively deflects the beam 906 in a "see-saw" motion to simulate the motion that each sensor 904 would undergo if attached to either side of an active catheter bending element. The sensors 904 were placed at opposite arms of a Wheatstone bridge (not shown) to obtain the difference between their responses. Because the resistance of the sensors 904 is low, 1.3 ohms, a relatively small input (220 mV) was used to the Wheatstone bridge.

Figure 14:
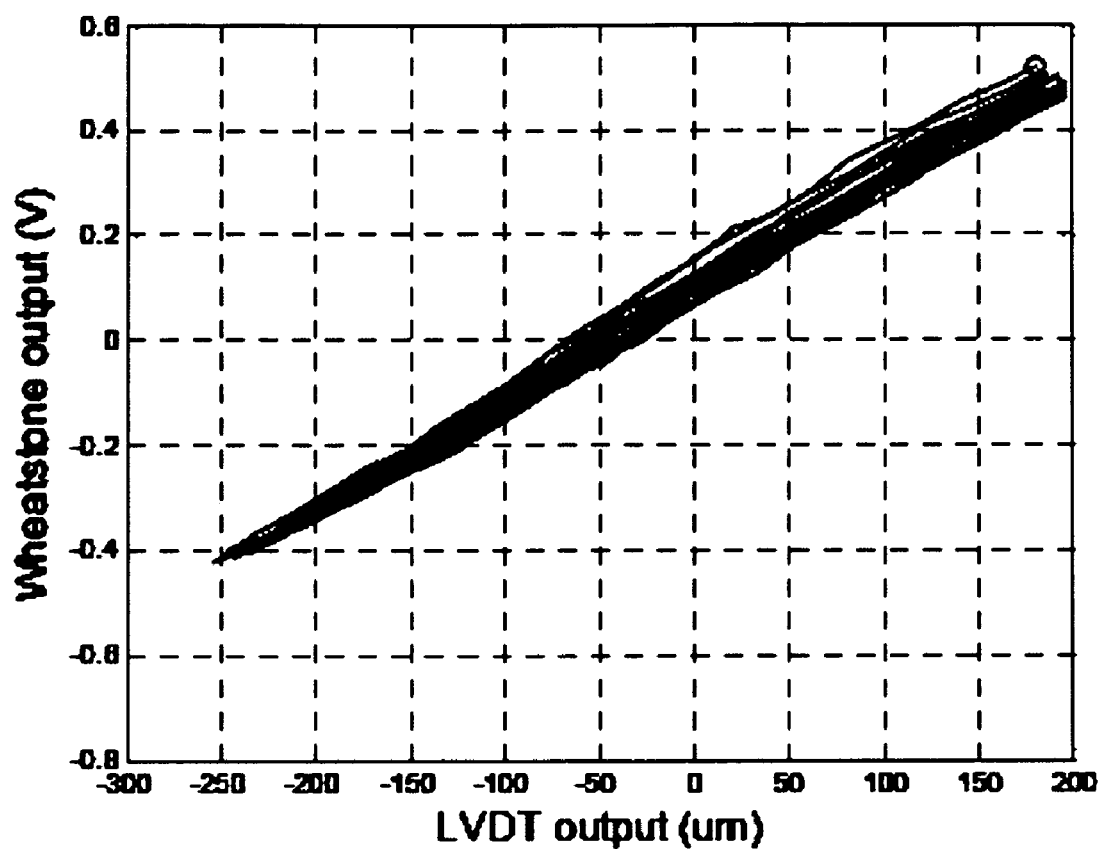
FIG. 14 shows results of a demonstration of sensors operating in a differential configuration, according to the current invention.

FIG. 14 shows results of this demonstration. The response is fairly linear over a number of cycles. There is some drift in the resistance measurement due to fatigue in the sensors 904. Because these sensors 904 were not well-optimized in this example, they undergo significant stress concentrations when stretched to their operating limit (near 30% strain), and this likely has caused residual strain to buildup. Despite this, the differential sensor was able to achieve a relatively linear output over 440 μm, or 20% of the sensor length. Each sensor operates between 10 and 30% elongation.

Figure 15:
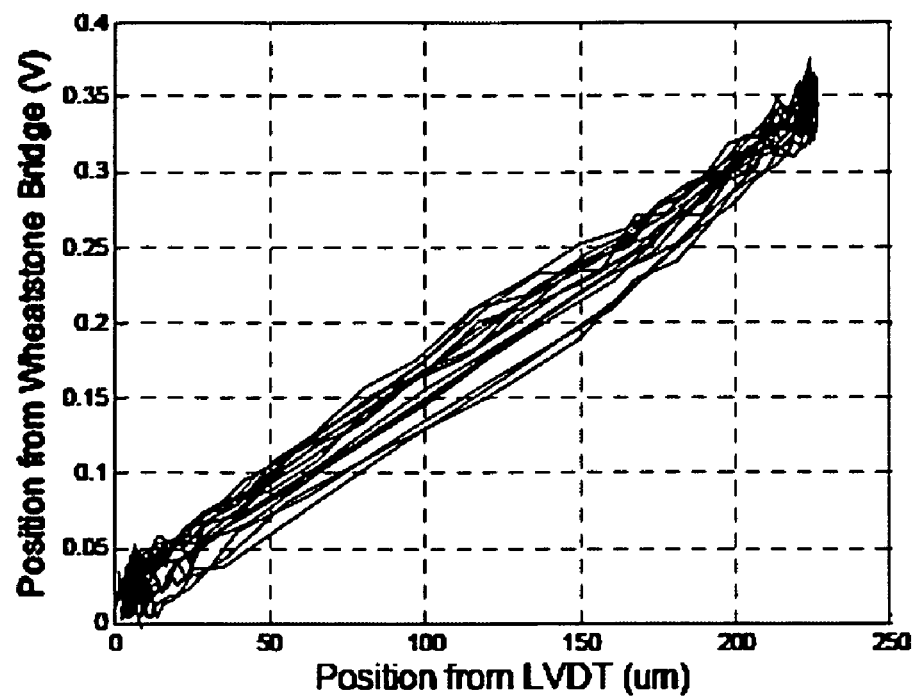
FIGS. 15(a)-15(c) show the results of a demonstration of sensors operating in a differential configuration under dynamic testing, according to the current invention.
Figure 15:
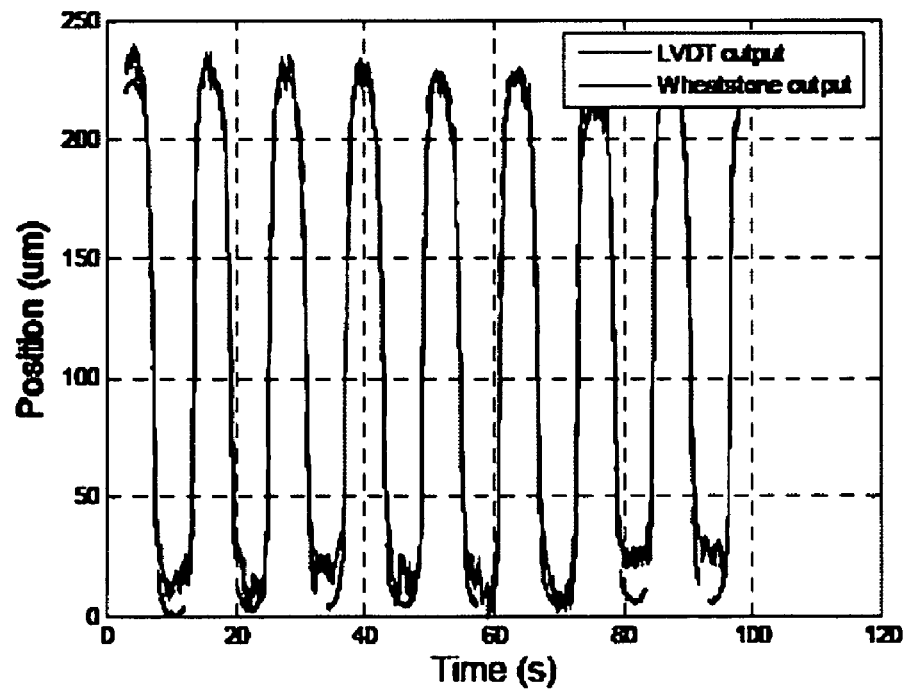
Figure 15:
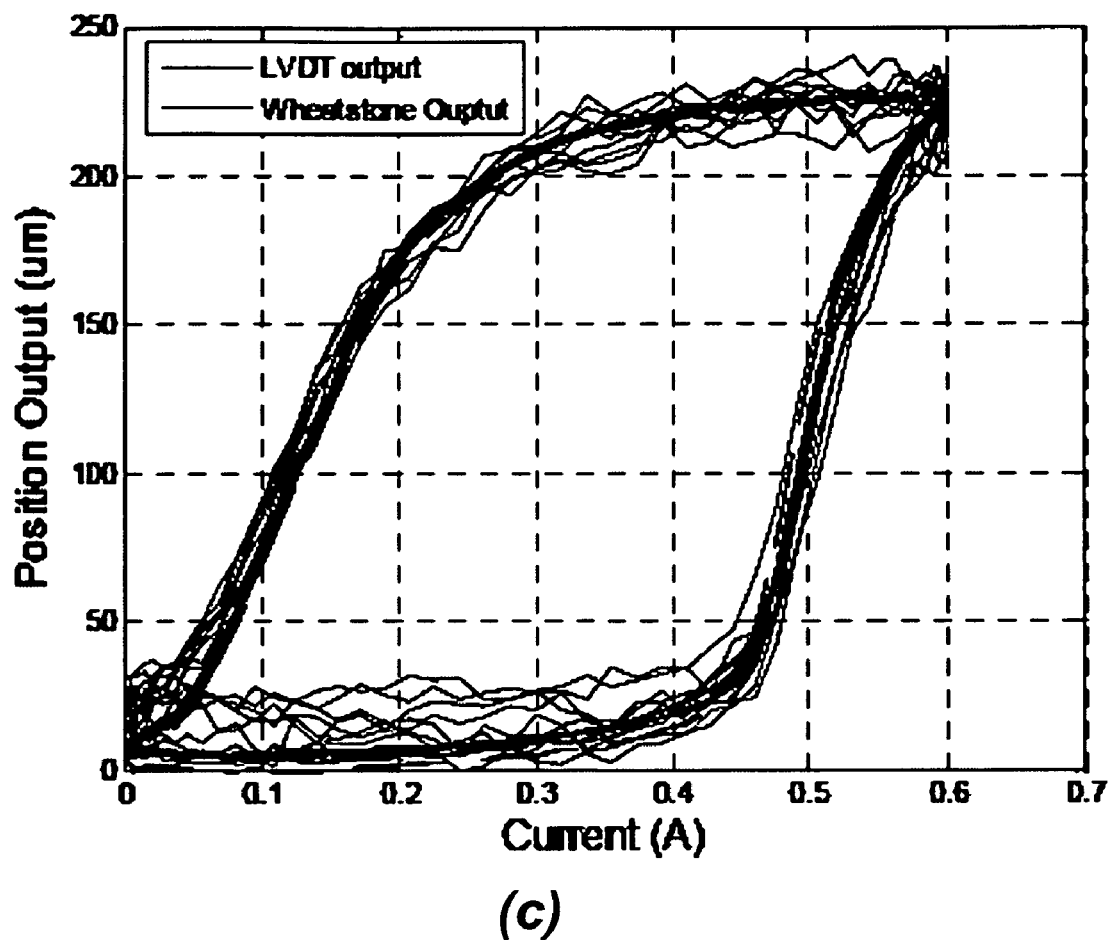

As a further example, the differential sensors are compared to the LVDT, under dynamic testing, in the setup of FIG. 9. Two sensors 904 were mounted on either side of the beam 906 as before, but also one SMA actuator 902 was mounted on one side with a static load on the other. A sinusoidal current was then passed through the SMA actuator 902 to cause it to deflect the weight. FIGS. 15(*a*)-15(*c*) show the results of these tests. FIG. 15(*a*) shows the SMA sensor 904 output through the Wheatstone bridge as compared to the LVDT output. It can be seen in the position vs. time data of FIG. 15(*b*), that the differential sensor 904 follows the LVDT 910 response relatively closely, although there are some significant variations at the top and bottom of each cycle. Here the SMA sensor 904 output has been scaled to closely match the output of the LVDT 910 for comparison. As before the relationship is relatively linear.

The position vs. current data in FIG. 15(*c*) shows the typical hysteresis response for a SMA actuator 902, and it is seen that the SMA sensor 904 is able to track the LVDT 910 response fairly well. The sensor 904 output is noisy, due to lack of additional filtering in this example.

The quasi-static testing shows that despite the differences in design geometries, the absolute resistance change and relative resistance change are of comparable values. The relative stiffness of the sensors is also similar.

The differential operation of the sensors yields more linear output and a larger output signal, and can reduce the effect of temperature fluctuations. With sensors that are within a small enough volume, any temperature perturbations generally affect both sensors equally and can be subtracted out by the differential configuration of the current invention. This works well to address fluctuations in local body temperature, for instance.

Figure 16:
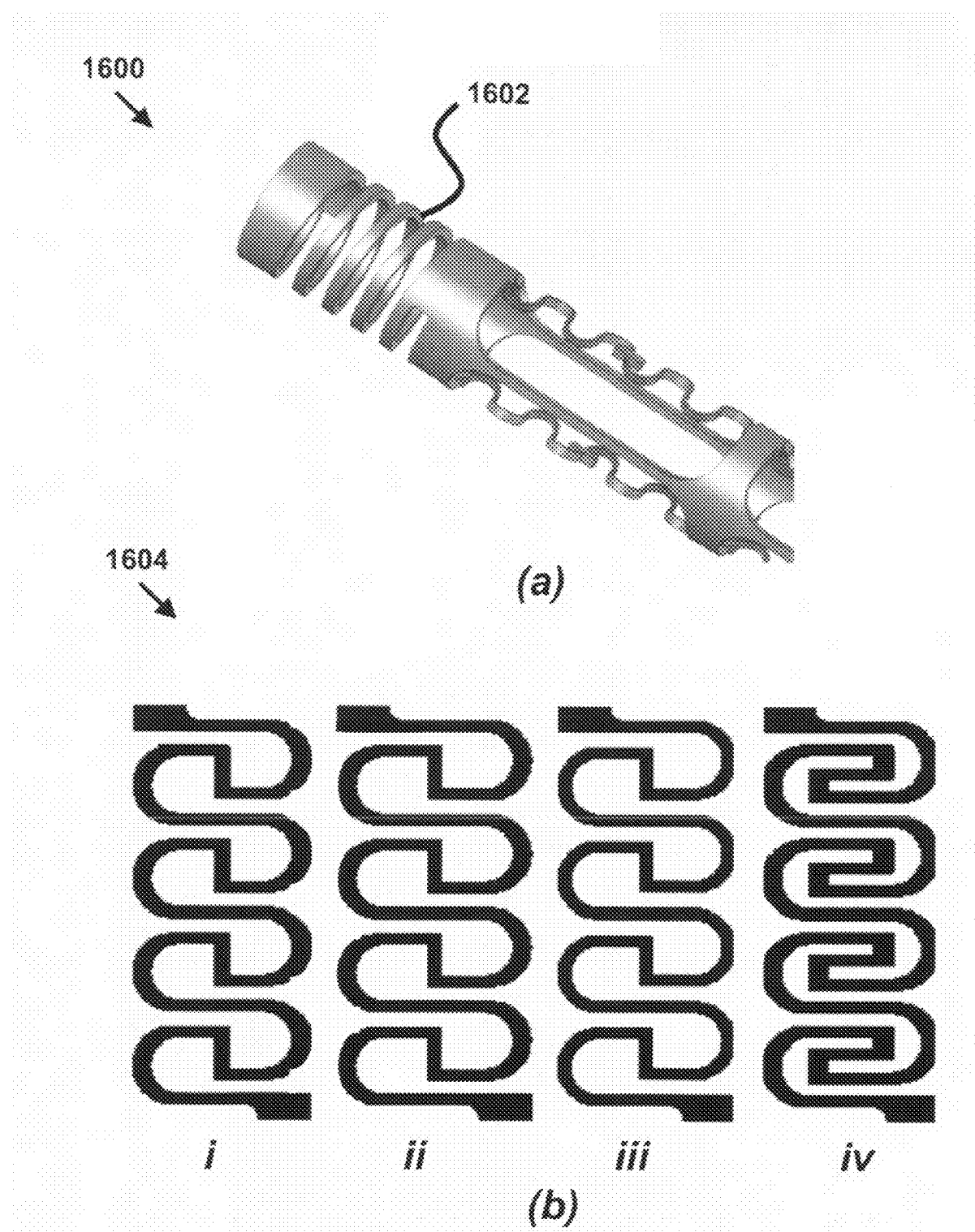
FIGS. 16(a)-16(b) section of tubing is laser-machined to create a force sensor having a compression spring shape, and exemplary sensors, respectively, according to the current invention.

In another embodiment, shown in FIGS. 16(a)-16(b), a section of laser-machined shape memory alloy tubing, in austenite phase, is added onto the tip of a typical interventional catheter to operate as a force sensor 1600. This section of tubing is laser-machined to have a compression spring shape 1602 that is fitted with at least one shape memory alloy strain sensor 1604 (such as one shown in i-iv of FIG. 16(b)), preferably on either side, and attached to the tip of the catheter (not shown). It should be understood that the strain sensors 1604 are for illustrative purposes and that many sensor patterns are possible to achieve the desired outcome. The whole structure, including the spring shape 1602 and sensors 1604, can be designed using finite element analysis. The strain sensors 1604 are prestrained and electrically isolated on at least one end as they are attached so that they can effectively measure the compression of the spring 1202 without buckling. The strain sensors 1604 are designed to be very compliant relative to the compression spring so that they can be prestrained without compressing the spring a significant amount. Here, the strain sensors 1604 have leads (not shown) attached to measure the change in electrical resistance of the sensor as it deflects. This embodiment is a compliant tip on a catheter (not shown) that, when the tip is compressed, the strain sensors 1604 also compress and the resistance of the strain sensors 1604 changes. A pre-calibrated spring constant can be used to translate the deflection of the spring into a force imparted on the tip. This force information can be relayed back to the physician through an electromechanical interface, visual cues, or other sensory methods (not shown). In this embodiment, the force sensor 1600 could be made to detect only axial forces by placing three strain sensors around the compression spring and taking the average of the responses among them. This would cancel out uneven deflection of the compression spring sensor. To obtain information about forces at the tip in directions other than the axial direction, three strain sensors can be mounted evenly spaced around the compression spring 1602 and differential information (as discussed above) is obtained from the sensors to determine the deflection angle of the compression spring 1602. With simple switching electronics, either mounted on the catheter as an integrated circuit or external to the catheter, the sensors could be read in axial (average) or lateral (differential) sensing mode. With proper calibration, this enables one to detect both lateral and axial forces at the tip of the catheter, which enables the physician to feel the approach angle of the catheter when contacting tissue.

Using this laser-machining technique according to the current invention, the mechanical characteristics of a force sensor 1600 can be adjusted to obtain the compliance desired for a force sensor while maintaining the small size and design flexibility needed for an application. Such a sensor can be laser-machined out of SMA tubing, which easily fits the form factor of a tubular catheter, and is easier to integrate than traditional strain gauges. This force sensor fits in a very small volume (<1 mm diameter), and its design is limited only by the minimum feature size of the laser machining process. The sensor detects very small forces (<100 mN) which is difficult for other force sensors. In addition, the sensor design is completely configurable to the desired application and can be modified easily through finite element analysis design and laser-machining.

To demonstrate this embodiment, the position of the tip is measured of a standard interventional catheter without an axial force sensor as it is perturbed in different directions by a static force. The catheter was fixed at 4 cm from the tip. The catheter tip was bent to pre-selected angle settings of 45°, 90°, 135°, and 180°. For each setting, the tip's deflection was measured against a fine grid under microscope as the tip was pulled with a 49 mN force in varying directions. The resulting displacement of the tip was recorded three times for each catheter configuration. Each set of curves corresponds to the path of deflection of the catheter tip when subjected to a 49 mN force exerted radially from the tip of the catheter in points around a circle.

Figure 17:
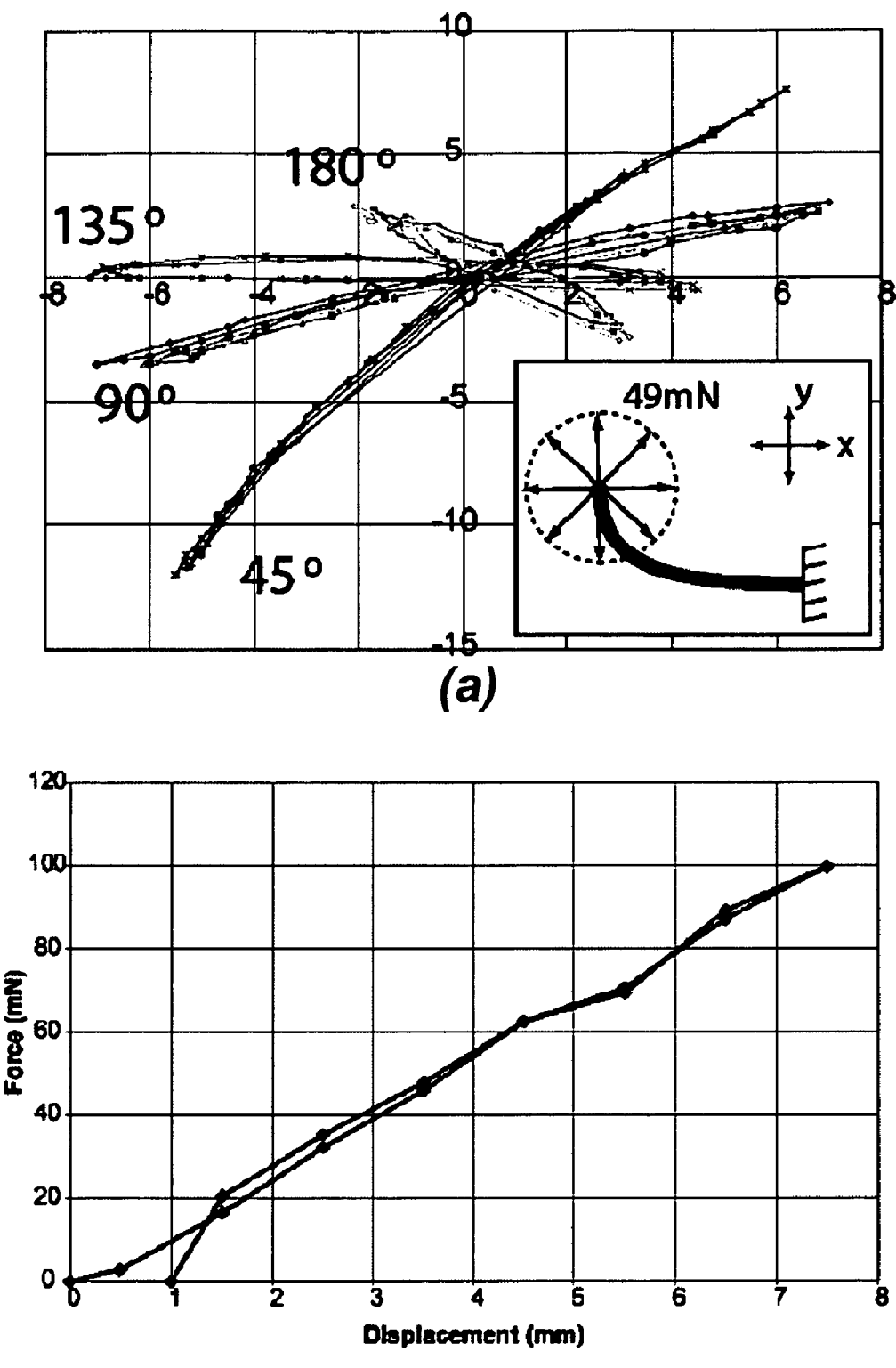
FIGS. 17(a)-17(b) show a graph of the position of a catheter tip with the catheter bent to varying degrees under static load applied varying directions, and a graph the force, respectively according to the current invention.

As seen in FIGS. 17(a)-(b), the tip displacement depends both upon the degree of bend in the catheter and the direction of the force. In general, a force applied parallel to the direction of the tip of the catheter causes significantly less displacement than a force applied perpendicular to the tip. Therefore, estimates of the force applied to the tip of the catheter from tip displacement will be significantly more accurate for forces in more lateral directions and relatively inaccurate for forces applied in axial directions for a given resolution of displacement measurement. For example when the catheter tip is kept at a 45-degree bend, little displacement of the tip occurs from forces applied axial to the tip.

FIG. 17(a) shows the position of the catheter tip with the catheter bent to varying degrees under static load applied varying directions. Each loop represents the path of the tip as the direction of force is changed throughout 360-degrees. The deflection curves are labeled with the degree of bending of the catheter. Zero-degrees corresponds to a straight catheter and 180-degrees is the catheter bent into a "U". The inset-illustration is of directions of applied force on catheter and an example of the catheter at 90-degree angle.

Varying the force for a given configuration yields a linear response with displacement, as shown in FIG. 17(b). Therefore, by measuring the difference in expected and desired positions of the catheter, magnitude of the external force applied to the catheter can be estimated and therefore the assembly can be used as a force sensor for forces applied in directions perpendicular to the catheter. In addition, because the active catheter of the inventors has position feedback along its length rather than just at the tip, information about forces imparted at points throughout the length of the catheter can be obtained.

Figure 18:
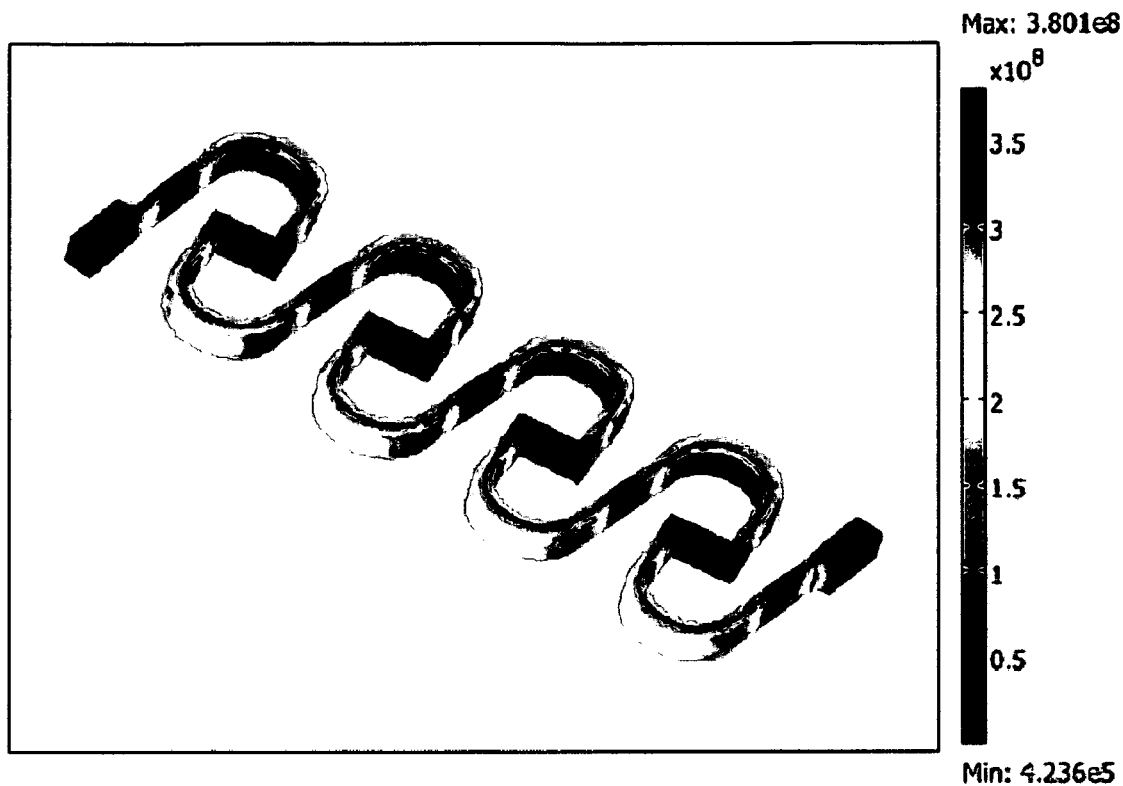
FIG. 18 shows an example of FEA modeling with the basic sensor design geometry shown in sensor of FIG. 16(b)(i), according to the current invention.
Figure 19:
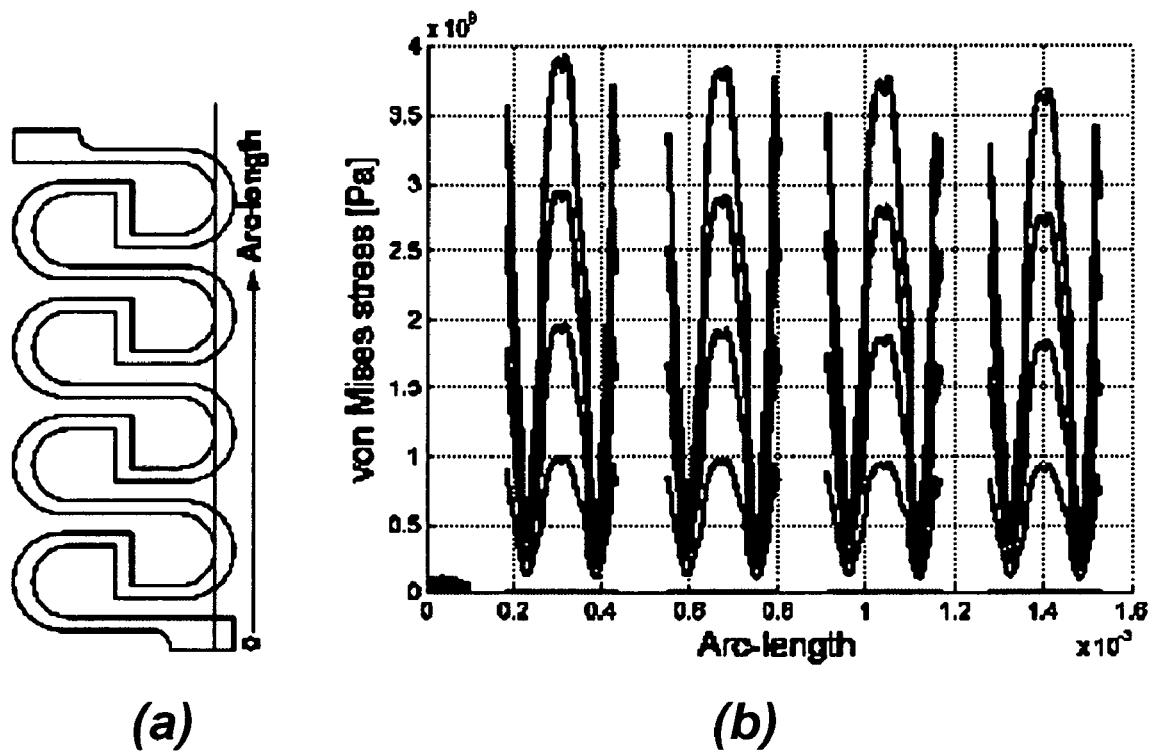
FIG. 19 shows stress concentrations, and the off-center connections in sensor of FIG. 16(b)(i), according to the current invention.

FIG. 18 shows an example of FEA modeling with the basic sensor design geometry shown in sensor of FIG. 16(b)(i), according to one embodiment of the invention. The vertical strut in the middle of each turn shortens the overall length of the structure by translating the bending moment at each turn. This also increases the path length and allows more turns in a smaller space. The curved turns reduce stress concentrations, and the off-center connections at the top and bottom reduce non-uniformity of stresses with successive turns, as shown in FIGS. 19(a) and 19(b). FIG. 19(b) shows the stress from FEA along the line in FIG. 19(a) for four different elongations up to 450 µm. As can be seen in FIG. 19(b), the peak stresses are roughly the same in each curve. Although many sensor designs are possible, this example focuses on showing variations of a single design to demonstrate the different tradeoffs when given a particular geometry. FIG. 16(b)(i-iv) show four example variations on the same basic design. The main differences are the width of the side curves, the overall width, and the path length. As seen in the FEA simulation results in Table 4, shifting these simple parameters can affect the absolute resistance, resistance change, and stiffness (estimated as the force at 450 µm elongation divided by 450 µm).

TABLE 4

SMA SENSOR FEA SIMULATED VALUES

| Design | Width | Side Curve | Resistance | ΔR | Stiffness |
|---|---|---|---|---|---|
| (i) | .68 mm | .07 µm | 1.46 Ω | .018 Ω | .138 mN/µm |
| (ii) | .75 mm | .07 µm | 1.63 Ω | .013 Ω | .097 mN/µm |
| (iii) | .68 mm | .06 µm | 1.65 Ω | .012 Ω | .075 mN/µm |
| (iv) | .68 mm | .07 µm | 1.89 Ω | .017 Ω | .131 mN/µm |

The design in FIG. 16(b)(i) shows the lowest absolute resistance but the largest resistance change. By widening the overall width in 16(b)(ii), the absolute resistance is increased and the stiffness is reduced, but at the sacrifice of resistance change. By decreasing the width of the side curves in 16(b)(iii), the absolute resistance stays the same as in 6(b) while both resistance change and stiffness are lower than 16(b)(iv). The design in 16(b)(iv) mimics 16(b)(i), but a winding section is added as a stiff member that increases the resistance without significantly decreasing the stiffness. This allows one to decouple the absolute resistance from the other parameters of the structure.

To demonstrate the efficacy of the current invention, the sensors are tested in quasi-static and dynamic conditions. The quasi-static tests allow characterization of the signal output of the sensors, their stiffness, as well as the variation due to the manufacturing process. The dynamic tests demonstrate the effectiveness of the sensor when used in single and differential configurations compared to a commercial position sensor.

For each of the four exemplary designs shown in FIG. 16(b)(i-iv), ten samples were tested using a tensile testing setup. Due to the quadratic resistance response, the sensors require some prestrain to achieve a useful operating region. Therefore, the SMA sensors were designed to function with the same prestrain (300 µm, or 20%) and displacement range (150-450 µm, or 10-30%) as the previously discussed SMA actuators. Each sensor sample was therefore extended from 0 to 450 µm elongation while measuring force and resistance.

To simulate the configuration of an active catheter, the sensors were also tested dynamically with the balanced beam setup discussed in FIG. 9. The resistances of one or two sensors are measured using a Wheatstone bridge configuration, coupled with an instrumentation amplifier and a separate 100 Hz single-pole filter with further amplification. Data is sampled using a data acquisition card and software. The SMA actuators were driven with sinusoidal inputs offset by 180 degrees.

Figure 20:
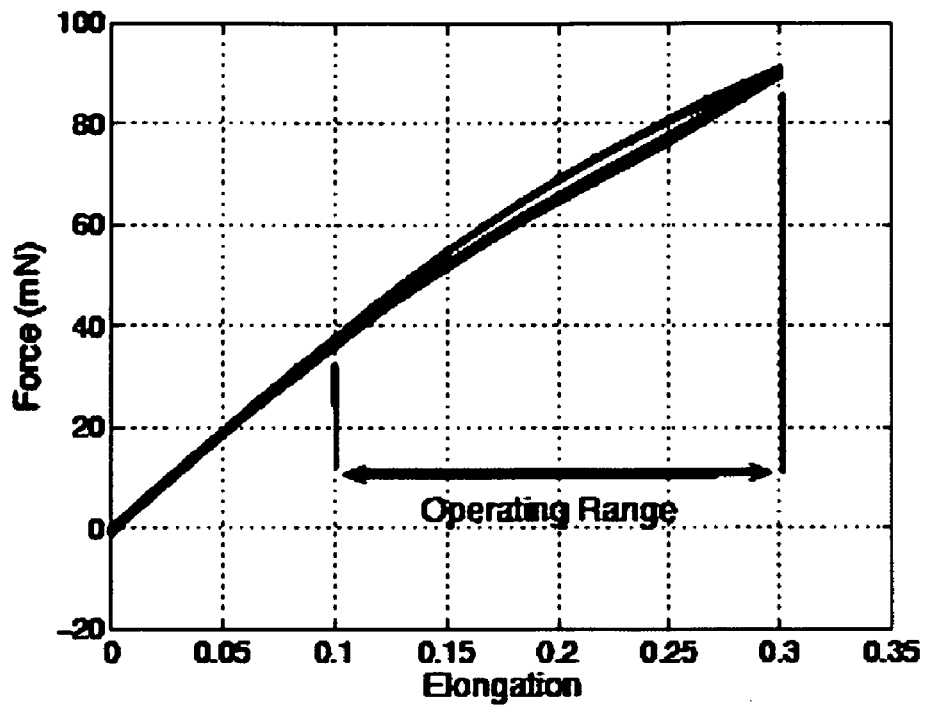
FIGS. 20(a)-20(b) show the measured force and resistance of one sample of sensor design of FIG. 16(b)(ii), according to the current invention.
Figure 20:
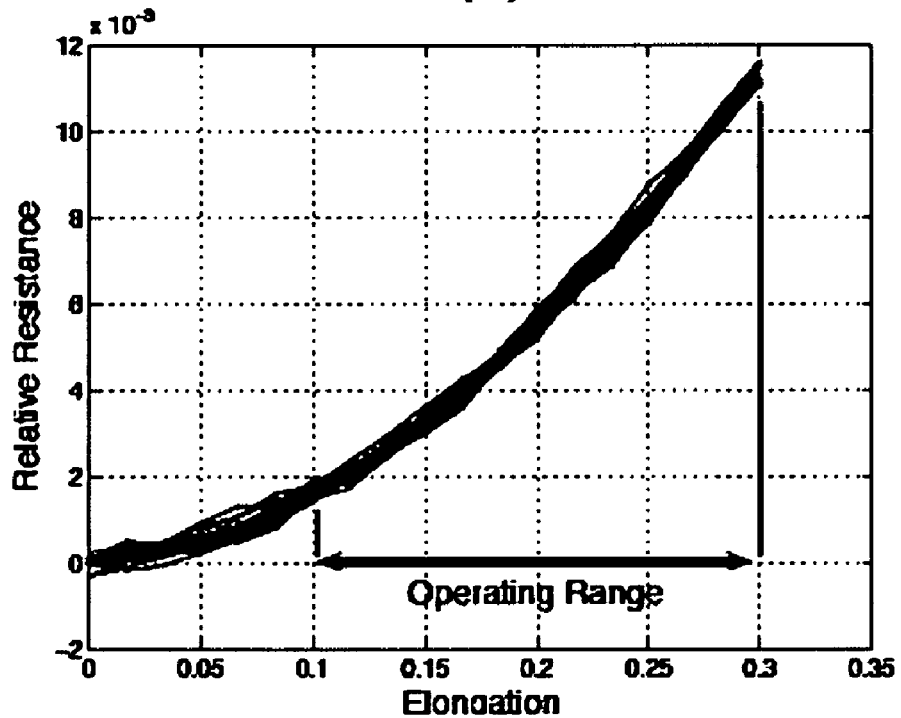

The quasi-static results were used to compare the performance of the different sensor designs. FIGS. 20(a) and 20(b) show the measured force and resistance of one sample of sensor design of FIG. 16(b)(ii) stretched to 30% elongation (450 µm) over 10 cycles. These tests were performed for 10 samples of each design and the data is compiled below. Because the value of the absolute resistance should correlate with the overall dimensions of the sensor, this is used as the independent axis of the following quasi-static graphs.

FIGS. 21(a) and 21(b) show the maximum percent resistance change for the four sensor designs at 30% elongation (450 µm) vs. the absolute resistance values as expected from the simulations. FIG. 21(b) shows the experimental results.

As seen in the figures, the experimental results follow the same basic trends as the simulated values, but there is some distribution due to manufacturing tolerances of the laser-machining process, as discussed below. Table 5 shows the simulated and average experimental relative change in resistance for each design. Each design is compared to the base design 6(a) for the simulated and experimental results. As the table shows, the simulation model predicts the relative trends in signal output among the sensor designs.

TABLE 5

SMA SENSOR SIMULATED VS. AVERAGE EXPERIMENTAL RESISTANCE VALUES

| Design | ΔR/R (Sim) | % Diff from (a) | ΔR/R (Exp) | % Diff from (a) |
|---|---|---|---|---|
| (a) | 1.22% | 0% | 1.51% | 0% |
| (b) | .82% | −33% | 1.16% | −23% |
| (c) | .94% | −23% | 1.23% | −19% |
| (d) | .70% | −43% | .95% | −37% |

The stiffness of the sensor is estimated by dividing the maximum force by the maximum displacement (450 µm). FIGS. 22(a) and 22(b) show the simulation and experimental stiffness results, respectively. The distribution of stiffness for each design is wider than that of the percent resistance change. Table 5 shows that the average experimental stiffness results do not follow the simulations as well as the resistance results do.

TABLE 5

SMA SENSOR SIMULATED AND AVERAGE EXPERIMENTAL STIFFNESS VALUES

| Design | Stiffness (Sim) | % Diff from (a) | Stiffness (Exp) | % Diff from (a) |
|---|---|---|---|---|
| (a) | $.138 \frac{mN}{\mu m}$ | 0% | $.253 \frac{mN}{\mu m}$ | 0% |
| (b) | $.096 \frac{mN}{\mu m}$ | −31% | $.222 \frac{mN}{\mu m}$ | −12% |
| (c) | $.104 \frac{mN}{\mu m}$ | −24% | $.182 \frac{mN}{\mu m}$ | −28% |
| (d) | $.131 \frac{mN}{\mu m}$ | −5% | $.180 \frac{mN}{\mu m}$ | −29% |

There are a number of reasons that the predictability of the relative force characteristics using this model will be less compared to that of the resistances. The perfectly plastic stress-strain model greatly simplifies the stress-strain response and does not account for hysteresis. In contrast, the resistance model is taken directly from experimental data and has no hysteresis. For this application, accurate modeling of the force characteristics is not necessary, as long as the sensor stiffness is low compared to that of the actuator. These exemplary sensors exhibit a maximum of 7% of the actuator stiffness.

As can be seen from FIGS. 20(a) and 20(b), despite the appearance of significant hysteresis in the mechanical characteristics, the electrical resistance showed little hysteresis. This is likely due to the difference in distribution of mechanical strains in the sensor structure and the distribution of the current density, which determines the overall resistance.

Figure 23:
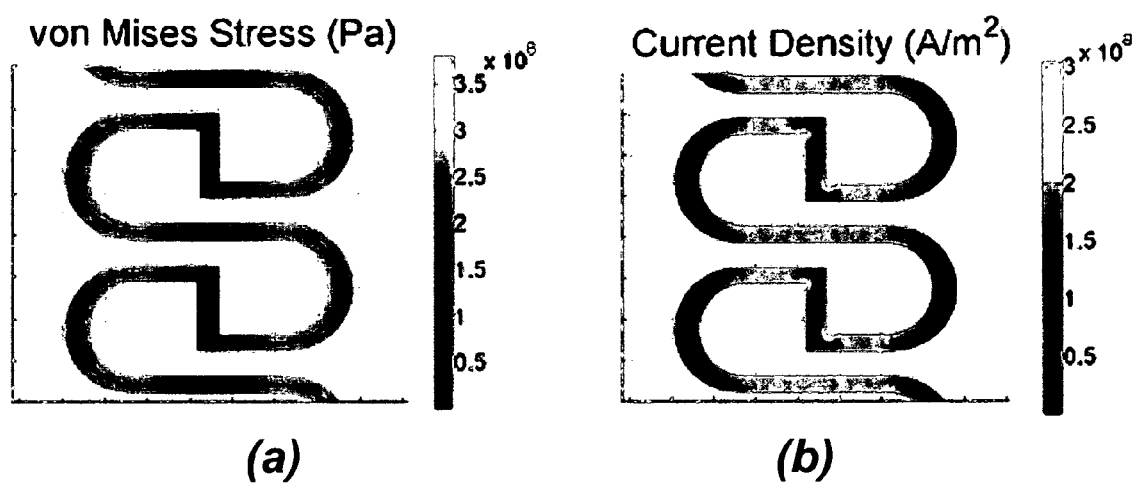
FIGS. 23(a)-23(b) show FEA simulations of the stress and current density in the sensor shown in FIG. 16(b)(i), according to the current invention.

The FEA simulations in FIGS. 23(a) and 23(b) show that the high stress areas appear toward the inside edges of the curves, while the high current density areas are in the horizontal struts. Therefore the measurement of resistance is somewhat decoupled from the mechanical response of the structure.

Figure 24:
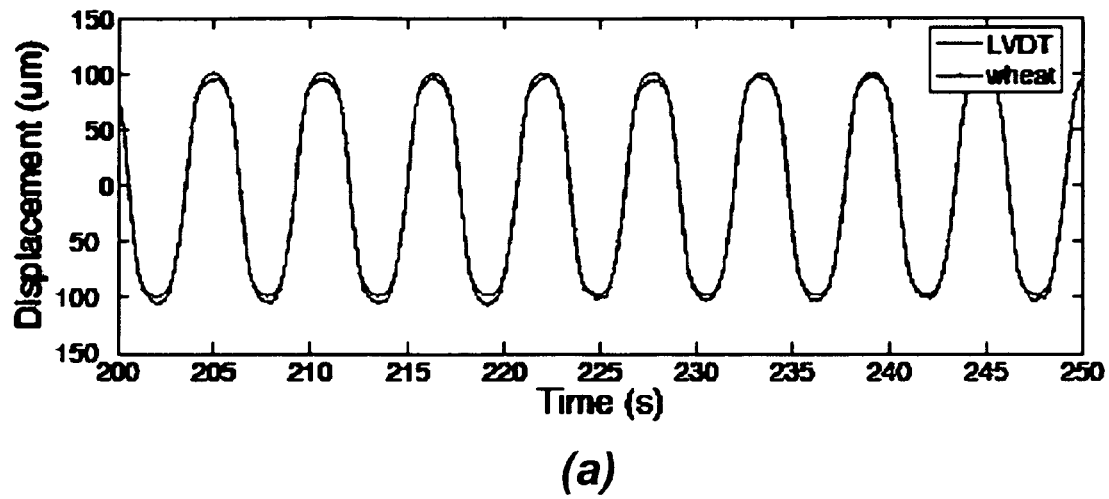
FIGS. 24(a)-24(b) show the LVDT output and the scaled Wheatstone output and the error between the two with one sensor of design 16(b)(iv), according to the current invention.
Figure 24:
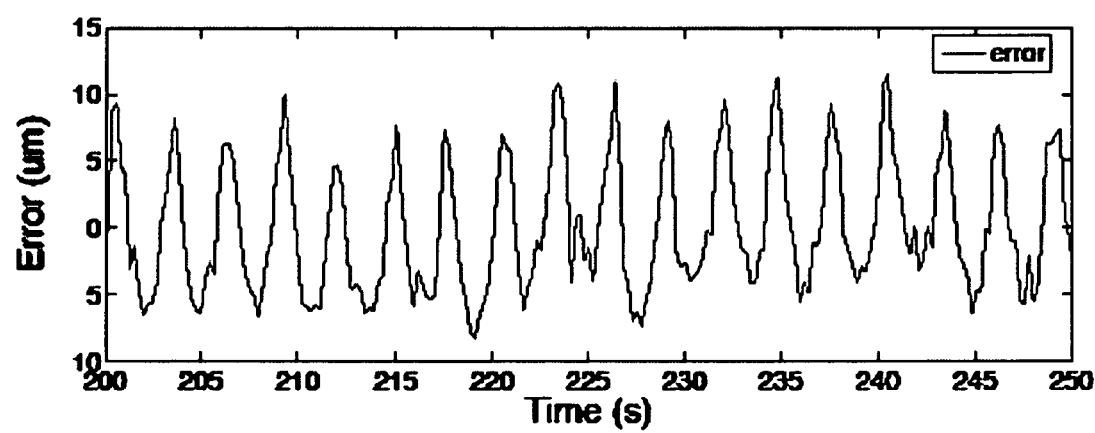
Figure 25:
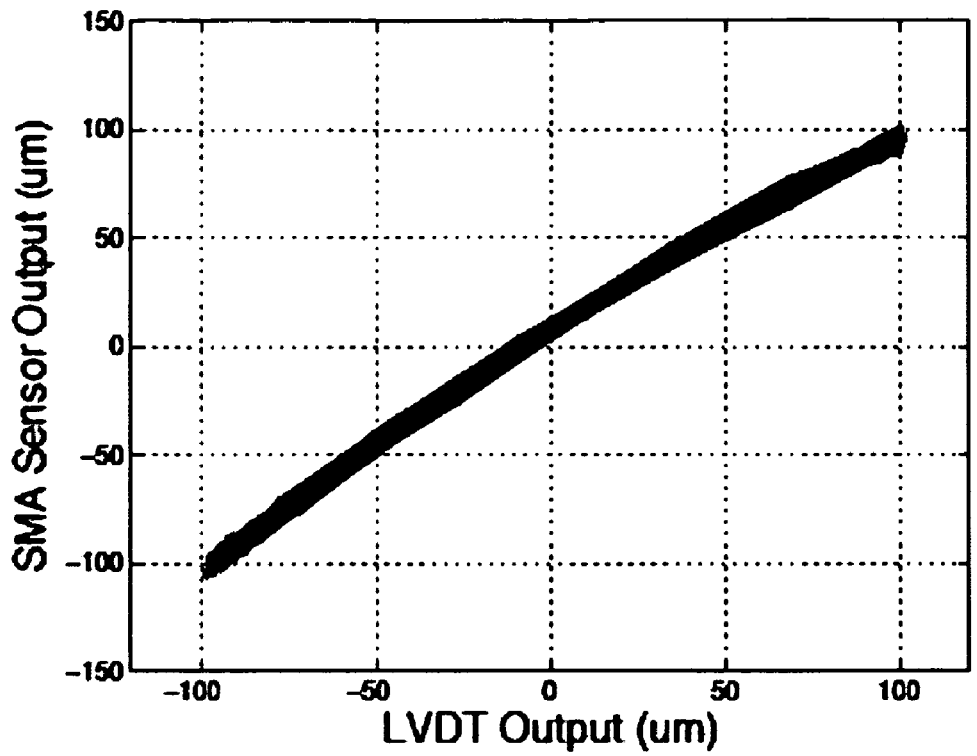
FIGS. 25(a)-25(b) show the scaled Wheatstone output vs. LVDT output with one sensor of design 16(b)(iv) in 25(a) and with two sensors of design 16(b)(iv) in 25(b), using the difference or the two sensor outputs, according to the current invention.
Figure 25:
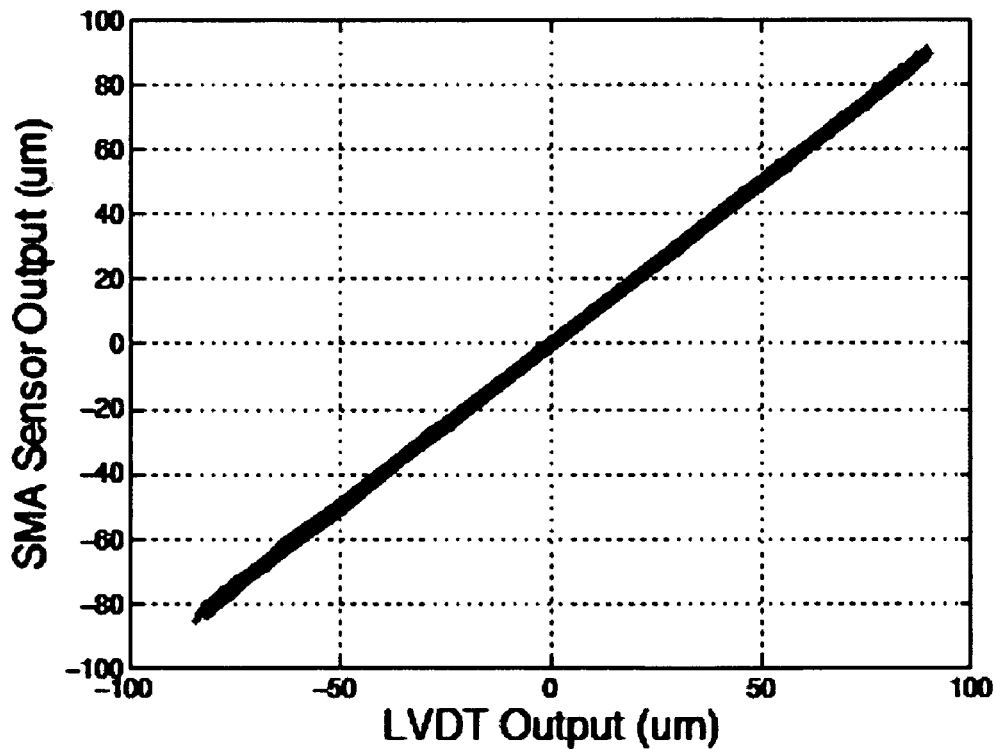

To demonstrate the sensors of the current invention in a more realistic configuration, dynamic testing of a single sensor is done when balanced with a static resistance and of two sensors in differential configuration. The LVDT output and the scaled Wheatstone output with one sensor of design 16(b)(iv) are shown in FIGS. 24(a) and 24(b) for a 0.3 A amplitude, 0.4 Hz sine input to the actuators. As seen in FIG. 25(a), the Wheatstone output is mostly linear with the LVDT output, though some curvature is apparent. The RMS error for one sensor compared to the LVDT is 4.9 µm, or 3.4% of full-scale, with a linear drift of 0.015 µm/s over 8-minutes and 200-cycles. The raw signal output for the single sensor configuration was ~6 mV/1 m from the amplification and filtering stage before scaling.

In differential configuration, the sensors exhibited a similar drift of 0.015 µm/s but with a lower RMS error of 0.91 µm, or 0.52% over 8-minutes. FIG. 25(b) shows the linear relationship between the Wheatstone output and that of the LVDT over a 174 µm range. The output is linear with the LVDT output. The raw signal output was ~9.6 mV/µm, which is 1.6 times the signal output of the single sensor. Although a single sensor can be used to track the position of an SMA actuator, the use of two sensors in a differential configuration improves the linearity of the output signal. It is possible that a differential configuration can produce twice the output signal if the sensors are perfectly balanced and linear. With some sensor nonlinearity and imbalance, the signal output was still 1.6 times that of the single sensor case. In addition, if the sensors are placed closely together as in an active catheter application, differential measurement can enable compensation for thermal fluctuations. Use of differential sensing also reduces the common-mode noise in the output and hence the RMS error. The sensor accuracy can be further improved with more complex signal conditioning or a frequency selective modulation scheme. The drift of the sensors is modest and can be compensated with proper calibration prior to use in an active catheter.

Figure 21:
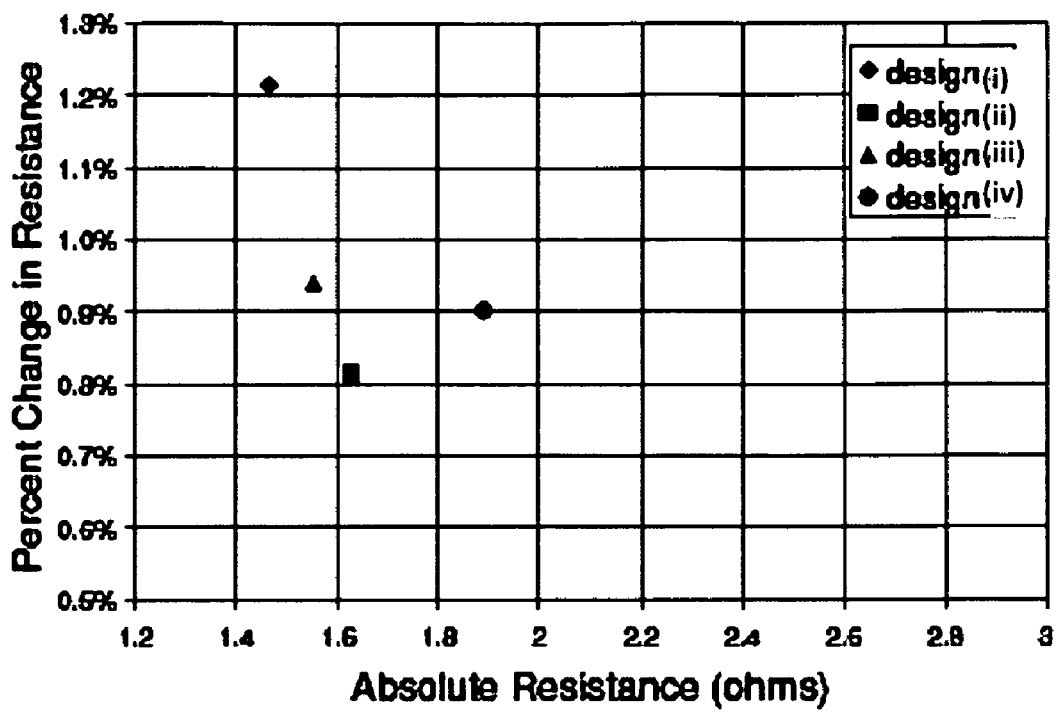
FIGS. 21(a)-21(b) show the maximum percent resistance change for the four sensor designs of FIG. 16(b), according to the current invention.
Figure 21:
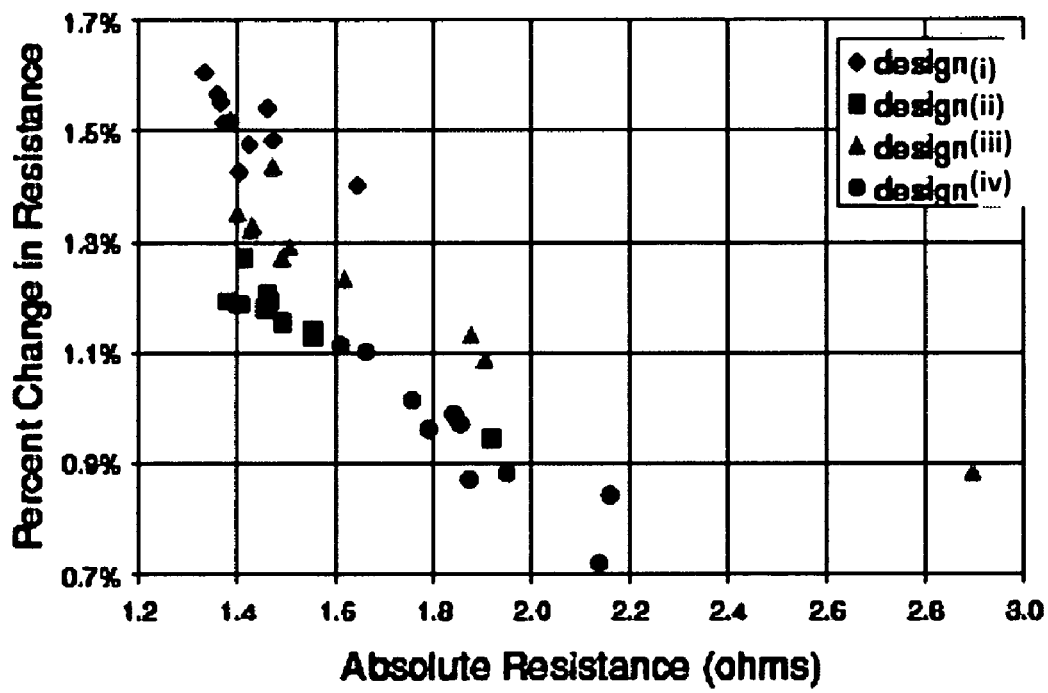
Figure 22:
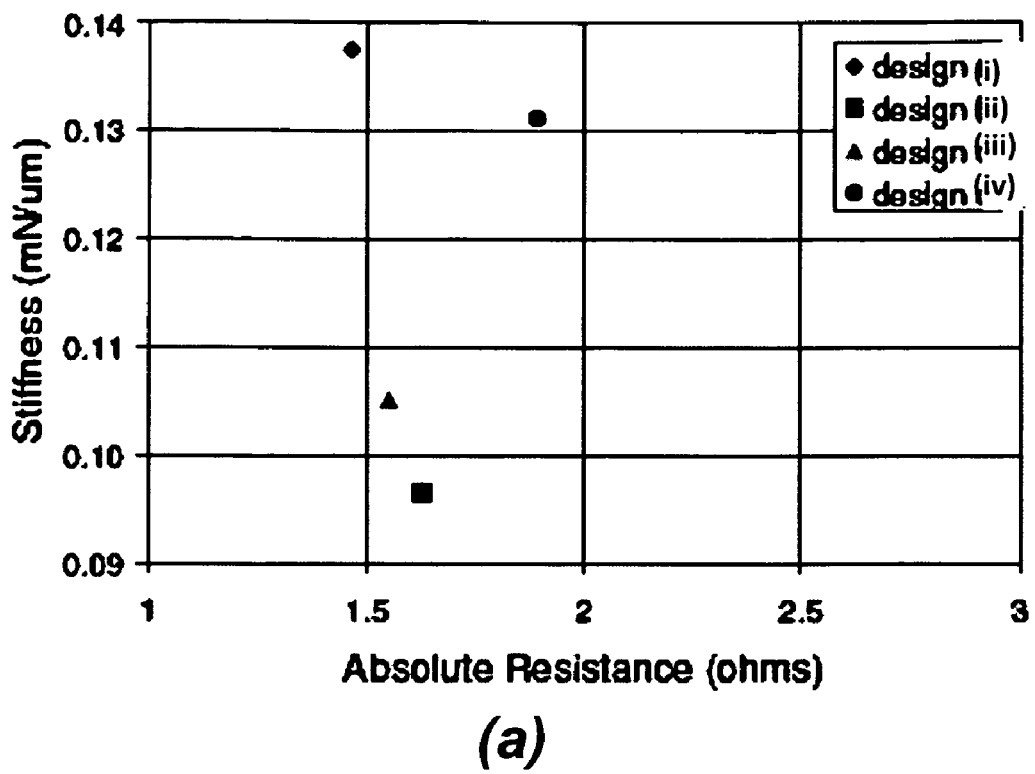
FIGS. 22(a)-22(b) show the simulation and experimental stiffness results for the four sensor designs of FIG. 16(b), according to the current invention.
Figure 22:
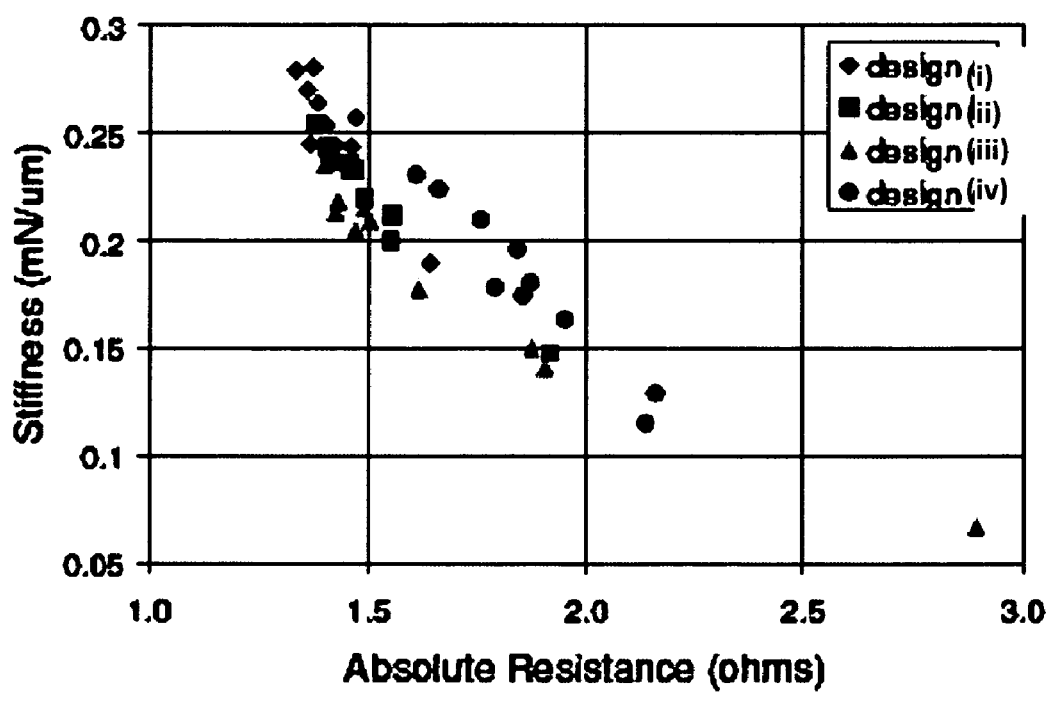

Manufacturing tolerances in the laser-machining process reduce the precision of the achievable dimensions and limit the ability of the FEA to predict the characteristics of an individual sensor. However, general trends corresponding to the design changes can be observed in most of the quasi-static results. As shown in FIGS. 21 and 22, the distributions of stiffness and resistance for design 16(b)(iv) were significantly wider than for the other designs, and the 16(b)(iv) results had larger deviation from the expected relative values. This is due to difficulties in obtaining repeatable cut dimensions with the more complex winding geometry.

Figure 26:
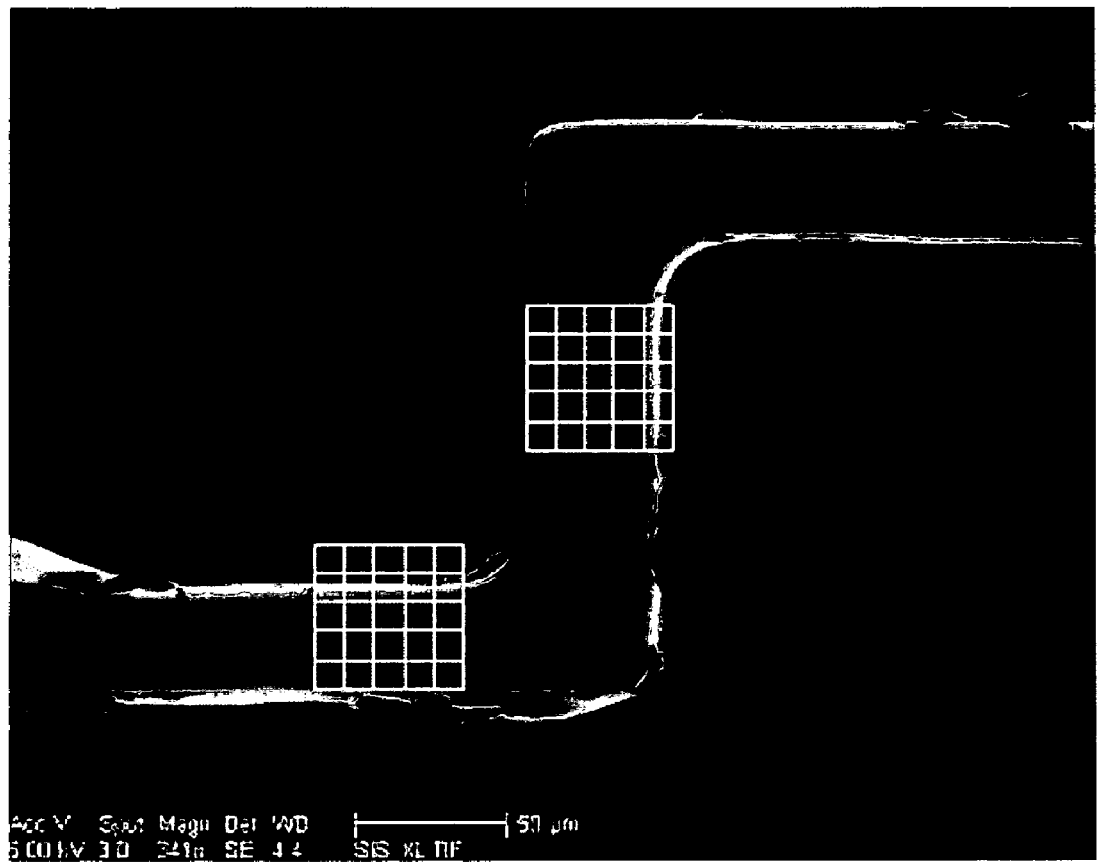
FIG. 26 shows a scanning electron microscope (SEM) image of a section of a sensor of the design shown in FIG. 16(b)(iii), according to the current invention.

As an example of the manufacturing variability, FIG. 26 shows a scanning electron microscope (SEM) image of a section of a sensor of the design shown in FIG. 16(b)(iii). The lower horizontal strut was designed to be 40 µm thick, and the vertical strut 50 µm. The actual dimensions are approximately 35 µm and 42 µm, respectively. The dimensions of these sensors are near the minimum limits of this laser-machining process, and so the machining tolerances can be quite wide. To mitigate these manufacturing issues, thinner tubing (or increased electropolishing) could be used to trade off the thickness of the tubing for strut thickness, which would allow for thicker struts that can be cut more precisely. The above data indicate, however, that the rapid cycling of FEA simulations and experimental verification can enable the design of sensors with the desired relative characteristics despite the manufacturing tolerances.

Figure 27:
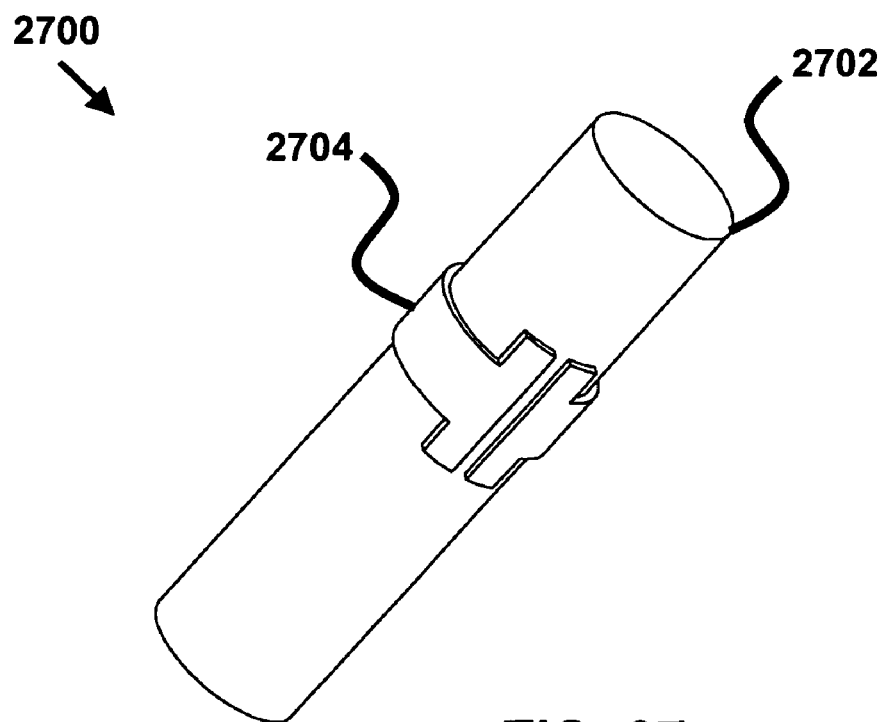
FIG. 27 shows a perspective view of a torsion sensor that wraps around a circumference of the catheter, according to the current invention.

The flexibility of the fabrication method allows for a variety of different kinds of sensors to be made. As shown in FIG. 27, the process can be used to create a torsion sensor 2700 that would wrap around the circumference of the catheter 2702, for instance, to measure torquing of the catheter 2702.

Figure 28:
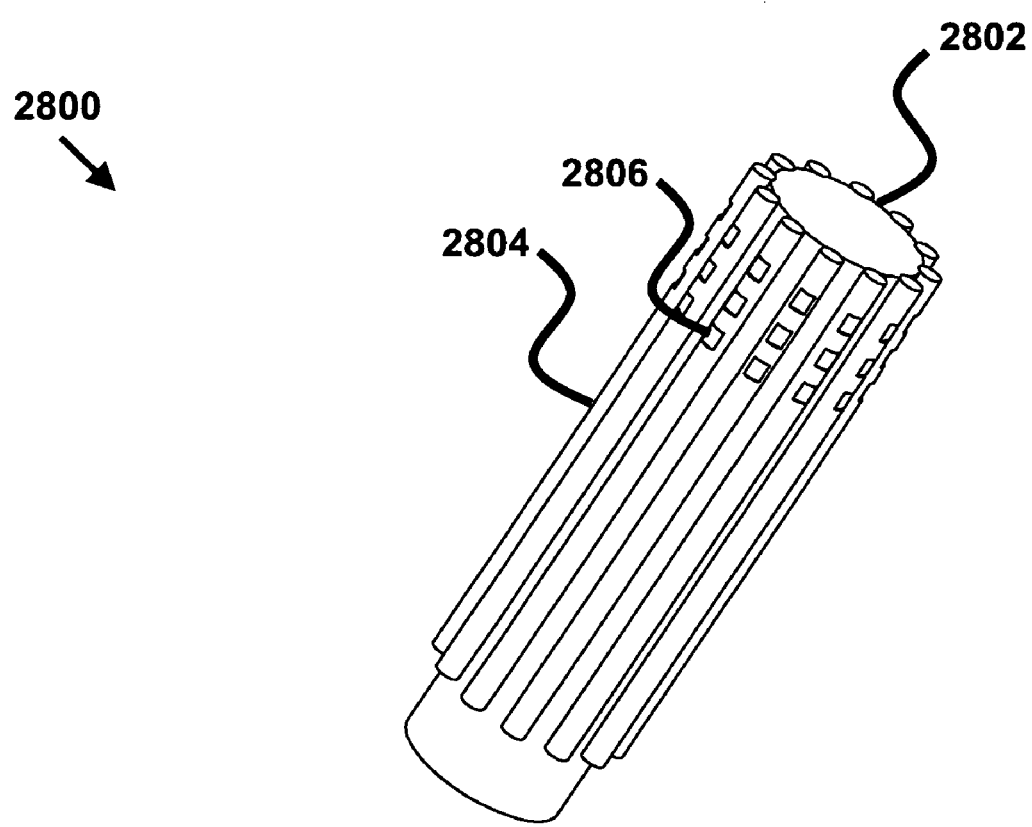
FIG. 28 shows a perspective view of sensor that includes a multi-core optical fiber having Bragg gratings along a length of the fiber, according to the current invention.

According to one embodiment of the current invention, the position-sensing device may include a multicore optical fiber with multiple Bragg gratings along its length 2800 as shown in FIG. 28. Here, an active catheter tip 2802 has fiber cores 2804 placed off-center within a circular cross section, and integrating several Bragg gratings 2806 along each core, the position-sensor detects strains in the Bragg gratings 2806 as the structure is flexed, where this information is used to calculate the position of the sensor along its length.

By inserting this position-sensing device 2800 into the lumen of a catheter (not shown), the position of the catheter tip 2802 relative to the proximal end of the sensing device can be determined. Because errors in the sensor output accumulate along its length, the Bragg gratings 2806 on the sensor can be confined to the active region of the catheter 2802 so that maximum accuracy is assured. Once incorporated, the position sensor 2800 can relay information about the catheter position to a computer controller, which can then be used to actuate the catheter under physician guidance.

Figure 29:
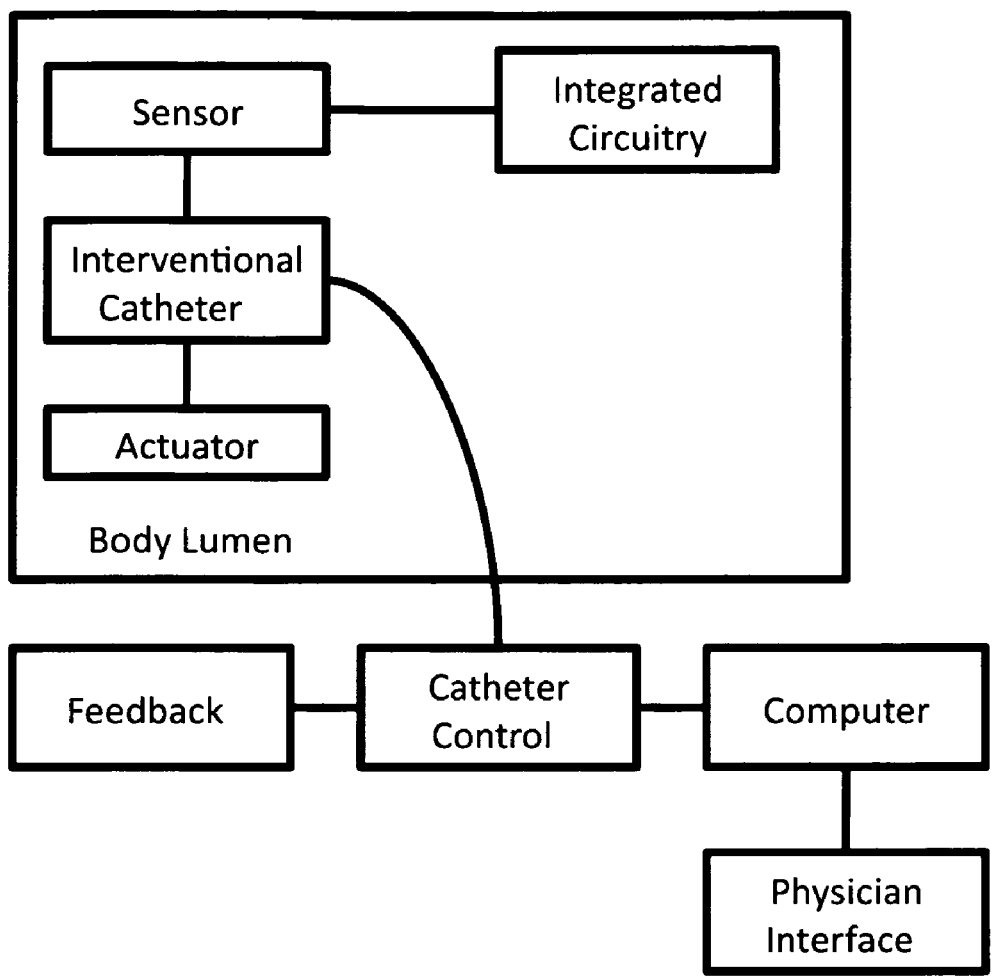
FIG. 29 shows schematic diagram of a haptic physician interface, where the interface includes an external replica catheter of the catheter within a patient, according to the current invention.

In another embodiment of the current invention, shown in FIG. 29, the physician interface can be a physical or virtual replica of the actual catheter that is within the patient. By manipulating this master catheter, the physician can control the slave catheter within the patient. Position sensing allows the slave catheter to sense perturbations from its environment and translate those to the master catheter. This aspect of the invention provides position sensing to allow a physician to feel forces being exerted by the environment around the catheter. This sensing ability on the catheter eliminates the need for the physician to only rely on poor two-dimensional visual feedback through biplane fluoroscopy. Current telerobotic systems cannot supply force feedback to the physician. According to one aspect of the invention, signal conditioning improves the sensor efficacy. In order to operate multiple actuators at once on the active catheter, on-board integrated circuitry is implemented to interrogate the position sensor. Clean amplification and filtering, coupled with sensors with a higher absolute resistance value, improves the quality of the signal output.

According to the current embodiment, the distributed position feedback systems for interventional catheters includes a catheter with maneuverable tip, a distributed position feedback system over at least part of the catheter, and a mechanical or virtual representation of the position feedback information. In one aspect, the distributed feedback system can be an optical sensing system, where the optical feedback system relies on fiber optic sensors with multiple Bragg gratings to detect bending in many directions. In a further aspect, the mechanical system can be enabled by a scaled-duplicate of the actual active portion of the catheter. A mechanical/virtual representation can be in the form of a virtual haptic interface, where the virtual representation can entirely reside in a 3D virtual environment, or the virtual representation can entirely reside in a 3D virtual environment where other devices are also represented and simulated. Alternatively, the virtual representation can entirely reside in a 3D virtual environment where the patient environment (e.g. vascular space) is also represented and updated either in real-time or as an imported structure. Further, the mechanical properties of the patient tissue can be inferred from the positional data and simulated.

In another aspect of the current embodiment, more than one catheter is represented, where two or more catheters have coordinated activities. Additionally, one of the catheters may have additional imaging capabilities, where the plane of the imaging catheter can be projected in the mechanical or virtual environment.

The present invention has now been described in accordance with several exemplary embodiments, which are intended to be illustrative in all aspects, rather than restrictive. Thus, the present invention is capable of many variations in detailed implementation, which may be derived from the description contained herein by a person of ordinary skill in the art. For example, in a distributed sensing system, a series of strain sensors can be used along the length of the catheter to provide the shape sensing capability. In addition, laser-machined shape memory alloy sensors out of nitinol tubing that can be used for this sensor application. Because the sensors can be cut out of tubing, they could be more easily mounted onto a catheter shape than strain gauges. In addition, they can be customized to have low stiffness so as not to perturb the catheter motion. Flex circuits can be used to connect the sensors together to transmit signals down the length of the catheter, or integrated circuits can be mounted on the flex circuit to pre-condition signals before transmitting to the control computer. In addition, integration of position sensing capability onto the catheter can enable force feedback to the physician, which has not been accomplished in similar interventional systems. In addition, the sensor can be laser machined out of SMA sheet or ribbon for planar applications. Placing a force sensor on the tip of a catheter, and using that sensor to feedback information to the physician is also new. In addition, a multiple-direction SMA-based tip force sensor is novel.

All such variations are considered to be within the scope and spirit of the present invention as defined by the following claims and their legal equivalents.

What is claimed:

1. A force and position sensor for active catheters, comprising:
    a. at least one active interventional catheter, wherein said interventional catheter comprises a first end and a second end, wherein said interventional catheter first end is inserted to a body lumen, wherein said interventional catheter second end is outside said body lumen;
    b. at least one serpentine shape force and position sensor, wherein said serpentine shape sensor comprises a material in a generally stable temperature and austenite state, wherein said serpentine shape sensor comprises a first electrode disposed at a first serpentine shape sensor end and a second electrode disposed at a second serpentine shape sensor end, wherein said force and position sensor is incorporated proximal to said interventional catheter first end, wherein an electrical resistance across said force and position sensor changes according to a displacement of said interventional catheter first end, wherein a measure of a force and a position on said interventional catheter first end is attained, wherein tactile force and position of said catheter first end is communicated from said interventional catheter first end to said interventional catheter second end, wherein said force and position sensor comprises a compression spring, wherein said spring is disposed at said first catheter end, wherein a resistance of said spring changes with strain, wherein said sensor detects axial forces at said first catheter end.

2. The force and position sensor of claim 1, wherein at least one additional said force and position sensor is disposed along said spring, wherein said additional force and position sensor is pre-strained and electrically isolated on at least one end, wherein a position of said catheter first end and a compression force on said first tube end is attained from a deflection angle of said spring.

3. The force and position sensor of claim 1, wherein said force and position sensor is laser-machined.

4. The force and position sensor of claim 1, wherein force information is relayed to a physician through a sensory method selected from a group consisting of electromechanical interface, haptic feedback, visual cues, visual renderings, and audible alerts.

5. The force and position sensor of claim 1 further comprising an on-board integrated circuit, wherein said force and position on said catheter first end is interrogated.

6. The force and position sensor of claim 5, wherein said integrated circuit reads said force and position sensors in an axial and a lateral sensing mode, whereby lateral and axial positions and forces are detected at said catheter first end.

7. The force and position sensor of claim 1, wherein a first opposing said force and position sensors is compressed and a second opposing said sensor is stretched, wherein a linear response signal is attained from a difference of said resistances of said sensors.

8. The force and position sensor of claim 1, wherein said force and position sensor is made from a tube of SMA, wherein said tube comprises:
    a. a first tube end, wherein said first tube end is incorporated proximal to said catheter first end; and
    b. a second tube end, wherein said second tube end is incorporated along said catheter, wherein said force and position sensor comprises a first force and position sensor end proximal to said first tube end and a second force and position sensor end distal from said first tube end, wherein said force and position sensor is laser machined.

9. The force and position sensor of claim 8 further comprising at least one actuator formed in said tube, wherein said actuator comprises a first actuator end proximal to said first tube end and a second actuator end distal from said first tube end, wherein said actuator displaces said first tube end from a central tube axis when heated, wherein a measure of a lateral force on said catheter is attained when a change in resistance is measured across said force and position sensor.

10. The force and position sensor of claim 9, wherein said actuator shape is selected from a group consisting of a generally linear shape, zigzag shape, double zigzag shape, and curled flat winding shape.

11. The force and position sensor of claim 8, wherein said force and position sensor is a shape selected from a group consisting of a curved shape, a serpentine shape, a serpentine shape having vertical segments therein, a Greek-key shape, zigzag shape, double zigzag shape, and curled flat winding shape.

12. The force and position sensor of claim 1, wherein said force and position sensor is a torsion sensor, wherein said torsion sensor wraps around a circumference of said catheter, wherein a measure of a torque force on said catheter is attained.

13. The force and position sensor of claim 1, wherein said force and position sensor further comprises a haptic physician interface, wherein said interface comprises an external replica catheter of said catheter within a patient, wherein said replica is manipulated by said physician to control said catheter within said patient and enabling said physician to feel forces being exerted by an environment around said catheter within said patient.

14. A force and position sensor for active catheters, comprising:
   a. at least one active interventional catheter, wherein said catheter comprises a first end and a second end, whereby said catheter first end is inserted to a body lumen, whereas said second end is outside said body lumen; and
   b. at least one force and position sensor, wherein said force and position sensor comprises a multi-core optical fiber having at least one Bragg grating along a length of said fiber, whereby said fiber cores are disposed off-center from a circular cross section of said catheter, whereas strains in said Bragg gratings are detected by a light source as said catheter is flexed and a position of said sensor along said length is determined, wherein tactile force and position of said catheter first end is communicated from said interventional catheter first end to said interventional catheter second end.

15. A position and force sensor for active catheters, comprising:
   a. a tube of said SMA, wherein said tube comprises:
      i. a first tube end;
      ii. a second tube end; and
      iii. a tube center axis, whereby said second tube end is incorporated to a tip of an interventional catheter;
   b. at least one actuator formed in said tube, wherein said actuator comprises a first actuator end proximal to said first tube end and a second actuator end distal from said first tube end;
   c. at least one sensor formed in said tube, wherein said sensor is in a stable temperature and austenite state and comprises a first sensor end proximal to said first tube end and a second sensor end distal from said first tube end, wherein said actuator displaces said first tube end from said axis when heated, whereby an electrical resistance across said sensor changes according to said displacement, wherein a measure of said position of said sensor and a measure of said force on said active catheter are attained according to said heating and said resistance;
   d. a compression spring, wherein said spring is disposed at said first catheter end, whereas at least one said sensor is disposed along said spring, wherein said spring sensor is pre-strained and electrically isolated on at least one end, wherein a position of said catheter first end and a compression force on said first tube end is attained;
   e. a multi-core optical fiber having at least one Bragg grating along a length of said fiber, wherein said fiber cores are disposed off-center from a circular cross section, wherein strains are detected in said Bragg gratings as said catheter is flexed and a position of said sensor along said length is determined; and
   f. a haptic physician interface, wherein said interface comprises a external replica catheter of said catheter within a patient, whereas said replica is manipulated by said physician to control said catheter within said patient and enabling said physician to feel forces being exerted by an environment around said catheter within said patient.

* * * * *